(12) United States Patent
Boone et al.

(10) Patent No.: US 12,016,720 B2
(45) Date of Patent: *Jun. 25, 2024

(54) MODULAR PHANTOM FOR ASSESSMENT OF IMAGING PERFORMANCE AND DOSE IN CONE-BEAM CT

(71) Applicants: The Regents of the University of California, Oakland, CA (US); Johns Hopkins University, Baltimore, MD (US)

(72) Inventors: John M. Boone, Fair Oaks, CA (US); Jeffrey H. Siewerdsen, Baltimore, MD (US); George W. Burkett, Jr., Davis, CA (US)

(73) Assignees: The Regents of the University of California, Oakland, CA (US); The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/118,651

(22) Filed: Mar. 7, 2023

(65) Prior Publication Data
US 2024/0016466 A1   Jan. 18, 2024

Related U.S. Application Data

(63) Continuation of application No. 17/136,686, filed on Dec. 29, 2020, now Pat. No. 11,642,094, which is a
(Continued)

(51) Int. Cl.
*A61B 6/00* (2006.01)
*A61B 6/40* (2024.01)
*A61B 6/58* (2024.01)

(52) U.S. Cl.
CPC ............ *A61B 6/583* (2013.01); *A61B 6/4085* (2013.01); *A61B 6/5258* (2013.01); *A61B 6/542* (2013.01)

(58) Field of Classification Search
CPC ..... A61B 6/583; A61B 6/4085; A61B 6/5258; A61B 6/542
See application file for complete search history.

(56) References Cited

U.S. PATENT DOCUMENTS

| 5,844,965 A | 12/1998 | Galkin |
| 11,642,094 B2 * | 5/2023 | Boone ............... A61B 6/583 |
| | | 378/207 |

(Continued)

FOREIGN PATENT DOCUMENTS

| GB | 2504258 A | 1/2014 |
| WO | 2016/048088 A1 | 3/2016 |
| WO | 2018/081420 A1 | 5/2018 |

OTHER PUBLICATIONS

International Search Report and Written Opinion in PCT Appln. PCT/US2019/039977 dated Oct. 2, 2019; 11 pages.
(Continued)

*Primary Examiner* — Courtney D Thomas
(74) *Attorney, Agent, or Firm* — Kilpatrick Townsend and Stockton LLP

(57) ABSTRACT

Embodiments provide a modular phantom that enables quantitative assessment of imaging performance (e.g., spatial resolution, image uniformity, image noise, contrast to noise ratio, cone-beam artifact) and dosimetry in cone-beam computed tomography (CT). The modular phantom includes one or more modules for various imaging performance tests that may be rearranged in the phantom to accommodate the design of various cone-beam CT imaging systems. The modular phantom includes one or more of a cone-beam module, an angled edge module, or a line spread module. The phantom may be inserted into a larger sleeve and be used to assess imaging performance and dosimetry in whole body CT imaging systems.

20 Claims, 15 Drawing Sheets

Related U.S. Application Data continuation of application No. PCT/US2019/039977, filed on Jun. 28, 2019.

(60) Provisional application No. 62/692,574, filed on Jun. 29, 2018.

(56) References Cited

U.S. PATENT DOCUMENTS

| | | |
|---|---|---|
| 2005/0141672 A1 | 6/2005 | Endo et al. |
| 2008/0219410 A1 | 9/2008 | Gunzert-Marx et al. |
| 2009/0190723 A1 | 1/2009 | Jang et al. |
| 2011/0176723 A1 | 7/2011 | Ali et al. |
| 2015/0084625 A1 | 3/2015 | Yin et al. |
| 2016/0278734 A1 | 9/2016 | Hong et al. |
| 2017/0347987 A1 | 12/2017 | Hong et al. |

OTHER PUBLICATIONS

The Phantom Laboratory; "Catphan 500(R) And 600 Manual" (product manual); Dec. 18, 2015; retrieved at https://static1.squarespace.com/static/5367b059e4b05a1adcd295c2/t/58b5cb7b8419c25b96cba228/1500473967372/catphan+500600+Manual.pdf on Sep. 9, 2019.

* cited by examiner

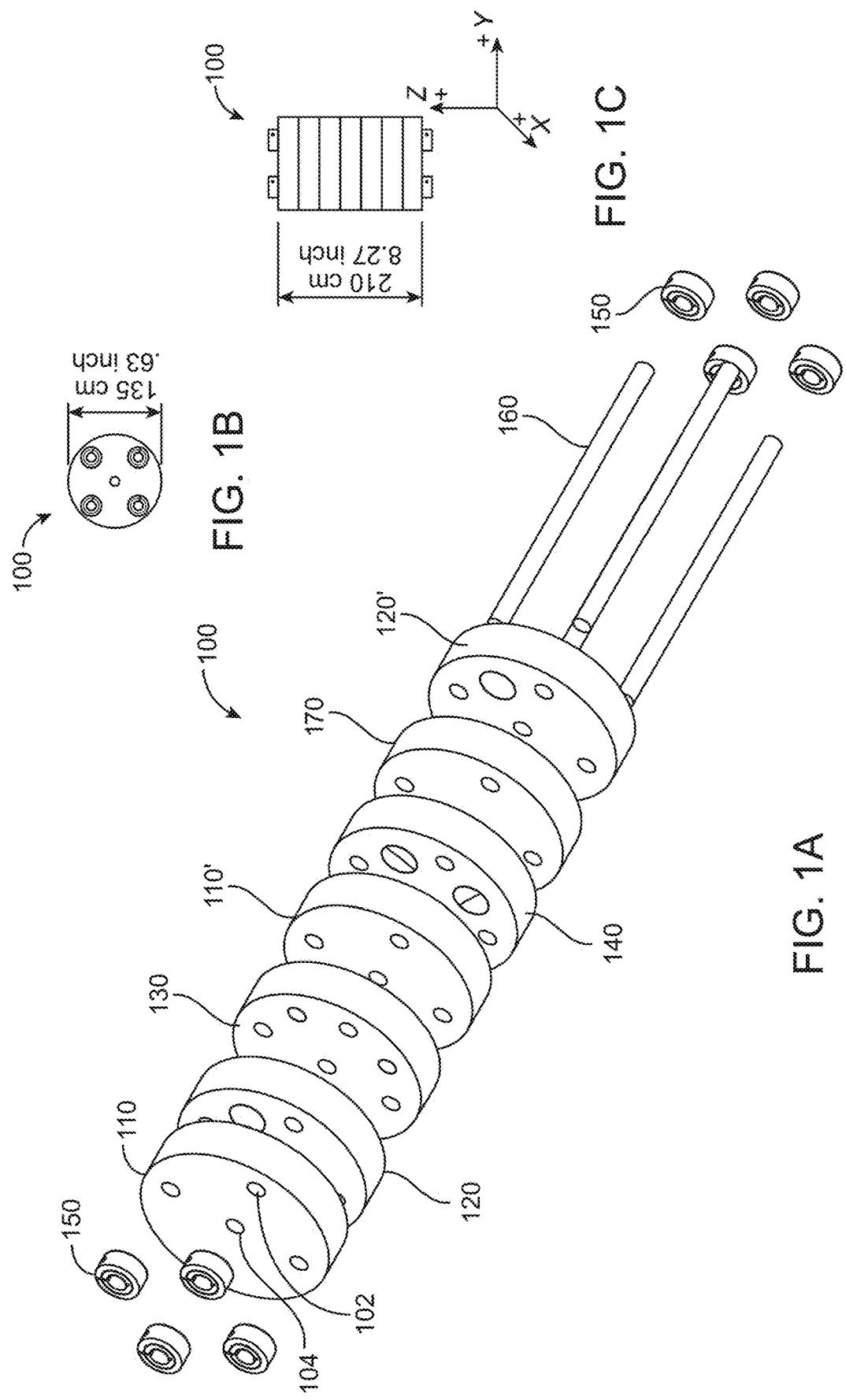

MODULAR PHANTOM FOR ASSESSMENT OF IMAGING PERFORMANCE AND DOSE IN CONE-BEAM CT

CROSS-REFERENCES TO RELATED APPLICATIONS

This application is a continuation of U.S. application Ser. No. 17/136,686 filed Dec. 29, 2020, which is a continuation of International Application No. PCT/US2019/039977 filed Jun. 28, 2019, which claims benefit under 35 USC§ 119(e) to U.S. Provisional Patent Application No. 62/692,574 filed Jun. 29, 2018, the disclosures of each which are incorporated by reference herein in their entireties for all purposes.

BACKGROUND

A medical imaging phantom is an object that is scanned or imaged to evaluate, analyze, and tune the performance of various imaging devices. A phantom provides more consistent results than the use of a living subject or cadaver, and avoids subjecting a living subject to repeated radiation exposure. Phantoms were originally employed for use in 2D X-ray-based imaging techniques such as radiography or fluoroscopy, though more recently phantoms with desired imaging characteristics have been developed for 3D techniques such as magnetic resonance imaging (MRI), computed tomography (CT), ultrasound, positron emission tomography (PET), and other imaging methods or modalities.

Existing medical imaging phantoms typically involve complex designs to enable subjective, qualitative assessment of image quality characteristics of a medical imaging device. Conventional phantoms are not capable of measuring the imaging performance and the dosimetry. Moreover, existing phantoms do not cover a range of imaging performance measurements and are not generally configurable in a manner suitable to a broad range of cone-beam CT scanner configurations. In addition, conventional phantoms are inconsistent with emerging standards for physical measurements for cone-beam CT accreditation in a number of ways, including overall dimensions (diameter and length) and in terms of including of test objects which permit the required measurements including conventional measurements and those specifically useful in cone-beam CT.

Embodiments address these and other technical problems, individually and collectively.

SUMMARY

Embodiments provide a modular phantom that enables quantitative assessment of imaging performance and dosimetry (i.e., measurement and assessment of ionizing radiation exposure levels delivered to the phantom during imaging) in cone-beam computed tomography (CT). The phantom includes one or more interchangeable and rearrangeable modules. The phantom provides a common, combined device for assessing imaging performance (for example, via the modules) and radiation dosimetry (for example, via one or more bore holes provided in the modules to accommodate the placement of an instrument at one or more positions in the modules).

The phantom discussed herein reflects an important design principle that stresses simplicity in physical design while emphasizing quantitative analysis which produces a number quantitative metrics which define image quality. The phantom according to various embodiments allows measurement of imaging performance and dosimetry within the same imaging system, using the same technique factors of the imaging system. According to various embodiments, the technique factors may include one or more of a tube potential (measured in kilovoltage (kV)), a tube current (measured in milliamperage (mA)), a time of exposure, and a system geometry of the imaging system (e.g., a field of view (FOV) of the imaging system, a source-axis-distance (SAD) of the imaging system, a source-detector-distance (SDD) (also called as a source-imager-distance (SID)), and an extent of the source-detector orbit) of the medical imaging device).

Embodiments provide a modular phantom for medical imaging and dosimetry comprising one or more modules ordered according to a predetermined order. The one or more modules include at least one of a cone-beam module configured to measure a cone-beam artifact for a medical imaging system, an angled edge module configured to measure at least one of a spatial resolution or contrast properties of the medical imaging system, or a line spread module configured to measure a line-spread function of the medical imaging system. The modular phantom is configured to measure an imaging performance of the medical imaging system including the modular phantom and a dosimetry of the medical imaging system. In some embodiments, the modular phantom may include a sleeve configured to envelop the one or more modules. The modular phantom may include at least one homogenous module.

In some embodiments, the modular phantom comprises two or more modules, and attachment means for attaching the two or more modules. The attachments means align the two or more modules. The attachment means include at least one supporting rod. Each module includes at least one through hole extending through the module, and through holes through a plurality of modules are aligned for receiving the at least one supporting rod.

In some embodiments, the imaging performance and the dosimetry of the medical imaging system are measured using a same set of technique factors for the imaging system. The set of technique factors include one or more of a tube potential, a tube current, a time of exposure, and a system geometry of the imaging system (e.g., a field of view (FOV) of the imaging system, a source-axis-distance (SAD) of the imaging system, a source-detector-distance (SDD), and an extent of the source-detector orbit) of the medical imaging device).

According to various embodiments, the modular phantom may include one or more through holes configured to receive one or more instruments for measuring the dosimetry of the medical imaging system. The one or more instruments include an ionization chamber.

In some embodiments, the modular phantom may include two or more of the same module. The modular phantom may include a first cone-beam module provided along a central axial plane of the modular phantom where a cone angle is zero, and a second cone-beam module provided at a predetermined distance of the central axial plane of the modular phantom where the cone angle is not zero. The predetermined distance of the central axial plane of the modular phantom is greater than 1 cm.

In some embodiments, at least one of the one or more modules includes a cavity adapted to receive an insert based on a medical imaging and dosimetry application associated with the modular phantom. The insert and a module comprising the insert are made of different materials. The cone-beam module includes at least one cavity, and an insert provided in the at least one cavity. The insert for the cone-beam module includes at least two components stacked along a z-direction of the cone-beam module. The angled edge module includes at least one cavity, and an insert provided in the at least one cavity. The insert for the angled edge module has at least one angled edge. The line spread module includes at least one cavity, and an insert provided in the at least one cavity. The insert for the line spread module includes a slit extending along a central line of the insert.

Embodiments also provide a medical imaging system comprising a radiation source configured to emit x-rays, a detector, and a modular phantom placed between the radiation source and the detector. The modular phantom includes one or more modules ordered according to a predetermined order, the one or more modules including at least one of a cone-beam module configured to measure a cone-beam artifact for the medical imaging system, an angled edge module configured to measure at least one of a spatial resolution or contrast properties of the medical imaging system, or a line spread module configured to measure a line-spread function of the medical imaging system. The x-rays emitted from the radiation source travel through the modular phantom before being received at the detector.

Embodiments further provide a method for measuring properties associated with a medical imaging system using a modular phantom including one or more modules ordered according to a predetermined order, the one or more modules including at least one of a cone-beam module configured to measure a cone-beam artifact for the medical imaging system, an angled edge module configured to measure at least one of a spatial resolution or contrast properties of the medical imaging system, or a line spread module configured to measure a line-spread function of the medical imaging system. The method includes determining one or more properties associated with an imaging performance of the medical imaging system to be measured. The method further includes identifying the predetermined order of the one or more modules based on the one or more properties to be measured. The method includes assembling the modular phantom based on the predetermined order; and placing the modular phantom between a detector and a radiation source of the medical imaging system. The method also includes collecting a first set of rays that are emitted from the radiation source on the detector after the rays travel through the modular phantom. The method further includes measuring the one or more properties associated with the imaging performance of the medical imaging system using the collected first set of rays; and measuring dosimetry of the medical imaging system using the collected first set of rays. Measuring the one or more properties associated with the imaging performance of the medical imaging system may further include measuring one or more of a spatial resolution, an image uniformity, an image noise, a contrast, a contrast to noise ratio, or the cone-beam artifact on the image acquired using the medical imaging system. In some embodiments, the method may include aligning at least one of the one or more modules with a central ray of the medical imaging system.

According to various embodiments, the method may also include removing the modular phantom from the medical imaging system; and assembling the modular phantom based on a different predetermined order into a modified modular phantom. The modified modular phantom may be placed between the detector and the radiation source of the medical imaging system. The method may further include collecting a second set of rays that are emitted from the radiation source on the detector after the rays travel through the modified modular phantom. The one or more properties associated with the imaging performance of the medical imaging system is measured using the collected second set of rays. The dosimetry of the medical imaging system is measured using the collected second set of rays.

Details of one or more implementations of the subject matter described in this specification are set forth in the accompanying drawings and the description below. Other features, aspects, and advantages will become apparent from the description, the drawings, and the claims. Neither this summary nor the following detailed description purports to define or limit the scope of the inventive subject matter.

BRIEF DESCRIPTION OF THE DRAWINGS

FIG. 1A illustrates a perspective view of an exemplary assembled modular phantom in accordance with embodiments of the invention;

FIG. 1B illustrates a top or bottom view of an exemplary assembled modular phantom in accordance with embodiments of the invention in accordance with embodiments of the invention;

FIG. 1C illustrates a side view of an exemplary assembled modular phantom in accordance with embodiments of the invention in accordance with embodiments of the invention;

DETAILED DESCRIPTION

Modular Phantom Design

Figure 1D:
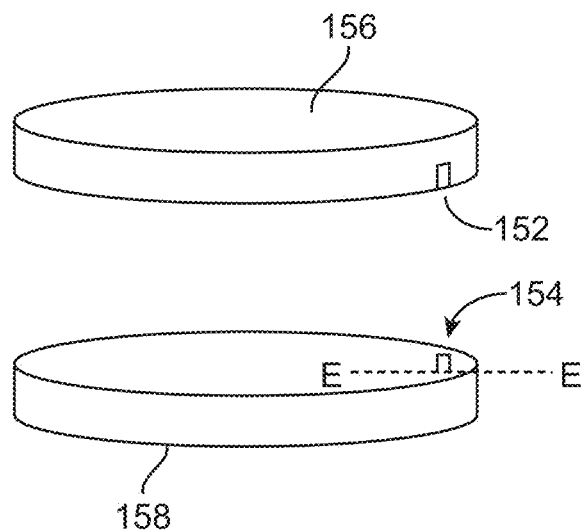
FIGS. 1D-1E illustrate exemplary attachment means for adjacent modules of a modular phantom in accordance with embodiments of the invention.

Embodiments provide a modular phantom that enables quantitative assessment of imaging performance (e.g., noise, noise variance, or noise power spectrum) of one or more medical images (e.g., a scan) acquired using a medical imaging system and dosimetry meter associated with the medical imaging system. For example, the medical imaging system may include a cone-beam computed tomography (CT) scanner or a whole-body CT scanner. The quantitative assessment of the imaging performance and the dosimetry associated with the imaging system may be accomplished using the same technique factors (e.g., a tube potential (measured in kilovoltage (kV)), a tube current (measured in milliamperage (mA)), a time of exposure, and a system geometry of the imaging system (e.g., a field of view (FOV) of the imaging system, a source-axis-distance (SAD) of the imaging system, a source-detector-distance (SDD) (also called as a source-imager-distance (SID)), and an extent of the source-detector orbit)) of the medical imaging device.

In some embodiments, the modular phantom may be sized and dimensioned based on the particular use or medical imaging system. For example, the modular phantom may be inserted in a sleeve. The sleeve may have any shape (e.g., a circular or elliptical annulus) with a hollow cavity for receiving the modular phantom therein. Accordingly, the interior portion of the resulting assembly containing the modular phantom may be smaller than the exterior portion of the assembly for the quantitative assessment of the imaging performance and the dosimetry associated with larger body sites or sizes. The sleeve may be configured to increase the diameter of the phantom (e.g. bulk up the phantom) to a diameter larger than the diameter of the various modules.

As used herein, a phantom may include a test object for medical imaging and dosimetry. The dosimetry may refer to the measurement, calculation and assessment of the ionizing radiation dose absorbed by the test object. According to various embodiments, the phantom may be a modular phantom including one or more modules. The one or more modules for various imaging performance tests may be rearranged in the modular phantom to accommodate the design of various medical imaging systems including, but not limited to, cone-beam CT systems. According to various embodiments, the phantom may be adapted to a variety of cone-beam CT imaging applications, including dental imaging, ear-nose-throat (ENT) imaging, orthopedic imaging, breast imaging, and interventional C-arms.

The modules for measuring the imaging performance of the medical imaging system include test objects suitable to assessment of spatial resolution in three spatial dimensions, image uniformity, image noise, contrast, contrast to noise ratio, and cone-beam artifact as well as radiation dose. The modules may also enable measurements that are consistent with emerging standards for physical measurements in cone-beam CT accreditation.

As used herein, spatial resolution may include the cut-off or Nyquist resolution that may refer to the smallest feature that can be distinguished in an image. The spatial resolution defined by the modulation transfer function (MTF) describes how well objects of different size can be seen. The MTF is commonly characterized in terms of the point-spread function (PSF), line-spread function (LSF), or edge-spread function (ESF). A separate MTF can be computed for each spatial direction (i.e., x, y, or z), or 2D and 3D MTFs can be computed combining directions.

As used herein, image uniformity may refer to the degree to which the signal in the image of a uniform, homogeneous object (e.g., a cylinder of water) is uniform (i.e., constant) throughout the object. In cone-beam CT, effects such as x-ray scatter, beam-hardening, and cone-beam effects may reduce the image uniformity.

As used herein, image noise may refer to fluctuations in the image that do not correspond to true variations associated with the object. The image noise arises from stochastic effects such as x-ray quantum noise or electronic readout noise. The image noise is commonly characterized in terms of the standard deviation of image values (within an otherwise homogeneous region of an object) and/or the noise-power spectrum (NPS) which characterizes not only the amplitude of the noise, but also the frequency dependence or "texture" of the noise.

As used herein, image contrast may refer to the difference in mean signal value between two regions (e.g., adjacent regions) in an image. For example, contrast may refer to the difference in image array scale between a region of acrylic and a region of polyethylene.

As used herein, contrast-to-noise ratio (CNR) is given by the image contrast (defined above) divided by the noise (defined above).

As used herein, the cone-beam artifact refers to a visual feature that appears on an image (acquired using a cone-beam CT scanner) of an object that is not present in the original object. That is, the cone-beam artifact may refer to an error in an image acquired with a particular imaging system. The cone-beam artifact may typically arise from 3D image reconstruction from data acquired in a circular orbit of a divergent ("cone") beam of x-rays and an area detector. The cone-beam artifact may be induced by discrepancies between the mathematical modeling and the actual physical imaging process. The presence of the cone-beam artifact in the acquired image may degrade the quality of the image to a non-diagnostic level.

Embodiments provide one or more modules that are configured to detect or measure one or more of the imaging performance elements of the medical imaging system as described above. The one or more modules include a cone-beam module configured to measure the cone-beam artifact generated (e.g. caused) by the medical imaging system, an angled edge module configured to measure at least one of a spatial resolution or the contrast properties of the medical imaging system, and a line spread module configured to measure the line-spread function of the medical imaging system. The line spread module may contain one or more slits with different slit widths, to accommodate CT systems with different resolving power.

According to various embodiments, the phantom may include two or more of the same (or nearly identical copies of) module. The modules may be rearranged along the length (e.g., in z-direction) of the phantom, depending on the needs of the assessment. According to various embodiments, the phantom may include any of the modules, (e.g., a cone-beam module configured to measure a cone-beam artifact for a medical imaging system, an angled edge module configured to measure spatial resolution and/or contrast properties of the medical imaging system, or a line spread module configured to measure a line-spread function of the medical imaging system), in any order along the long axis of the phantom. The modules are described below in greater detail.

FIG. 1A illustrates a perspective view of an exemplary modular phantom 100 that includes a plurality of modules such as a uniform module 110, a cone-beam module 120, a line spread module 140, and an angled edge module 170. According to various embodiments, the modular phantom 100 may include more or less modules. In some embodiments, the modular phantom 100 may include a single module, while in other embodiments the modular phantom 100 may include multiple modules. The exemplary modular phantom 100 illustrated in FIG. 1A also includes more than one of the same module, such as the uniform modules 110', and the cone-beam module 120'. FIG. 1B illustrates the top view of the modular phantom 100 and FIG. 1C illustrates a side view thereof. According to various embodiments, the modular phantom 100 may be coupled to a medical imaging system, and may be configured to measure an imaging performance and a dosimetry of the medical imaging system using a same set of technique factors (e.g. a tube potential, a tube current, a time of exposure, and a system geometry (e.g., a field of view (FOV) of the imaging system, a source-axis-distance (SAD) of the imaging system, a source-detector-distance (SDD), and an extent of the source-detector orbit of the medical imaging system).

The modules of the modular phantom 100 may be ordered according to a predetermined order. The predetermined order of the modules in the modular phantom 100 may depend on the use of the phantom. For example, the modular phantom 100 may include the line spread module 140 aligned with the central ray of a CT scanner to optimize the evaluation of spatial resolution in the (x, y) plane of the imaging system. The central ray of an imaging system may refer to the ray containing the x-ray source and intersecting the detector at a right angle. In some embodiments, the modules may be removed from the modular phantom 100 and reordered before being assembled again in form of the modular phantom. The order of the modules within the modular phantom 100 is discussed below in greater detail.

It may also be necessary to include more than one of the same module in the modular phantom depending on the desired measurements to be performed using the modular phantom. For example, a first cone-beam module may be provided along a central axial plane of the modular phantom where a cone angle is zero (i.e. the first cone-beam module is placed in the plane of the x-ray source), and a second cone-beam module may be provided at a predetermined distance (e.g., greater than 1 cm) of the central axial plane of the modular phantom where the cone angle is greater than or less than zero (i.e. the second cone-beam module is placed at the predetermined distance from the plane of the x-ray source, such as near the end of the field of view along the z-axis).

The modules of the modular phantom 100 may be kept together using any type of attachment means including but not limited to fasteners, support rods, removable adhesives, a sleeve covering the modular phantom, etc. Different type of attachment means may be used together. For example, the modular phantom may include one or more support rods, and may be inserted into a sleeve. The attachment means may be used to keep the modules together. The attachment means may also align the modules, if required for the particular use of the modular phantom.

For example, the modules of a modular phantom may be held together using one or more support rods 160, as illustrated in FIG. 1A. The support rods 160 can be inserted into through holes (e.g., apertures) 102 that extend through the modules. In some embodiments, through holes 102 of plurality of modules may be aligned for receiving a supporting rod 160. The support rods 160 keep the modules together and prevent slipping/sliding of one module with respect to other modules.

The modular phantom 100 may also include a plurality of fasteners (e.g., shaft collars, end plates, lids) 150 provided at opposite ends of the modular phantom 100, as illustrated in FIG. 1A. The fasteners 150 may be configured fix the modules in place. For example, the fasteners 150 may couple to the support rods 160. In the exemplary embodiment illustrated in FIG. 1A, the modular phantom 100 is held together with four fasteners 150 provided at a first end, and four additional fasteners 150 provided at a second, opposite, end of the phantom 100. The fasteners 150 are coupled to four support rods 160 at each end. One of ordinary skill in the art will understand that any number (including zero) and type of attachment means and any number (including zero) and type of fasteners may be used in connection with the modular phantom described herein. The attachment means and fasteners illustrated in FIG. 1A are for illustrative purposes only and should not be interpreted as limiting.

Figure 1E:
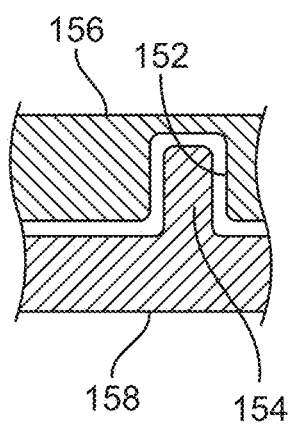

FIGS. 1D-1E illustrate an alternative exemplary attachment means (e.g., a peg and a hole attachment) for adjacent modules. The peg-and-hole attachment means may restrict the rotation of adjacent modules with respect to each other while keeping the adjacent modules together.

As illustrated in FIG. 1D, a first module 156 may include a cavity 152, and a second module 158 (adjacent to the first module 150 in the modular phantom 100) may include a protrusion 154. As illustrated in FIG. 1E, the protrusion 154 of the second module 158 may be shaped and dimensioned to fit into the cavity 152 of the first module 156. Similarly, the cavity 152 of the first module 156 may be sized and dimensioned to receive the protrusion 154 of the second module 158. When assembled in the modular phantom 100, the protrusion 154 of the second module 158 may be inserted into the cavity 152 of the first module 156, thereby attaching the second module 158 to the first module 156.

According to various embodiments, each module may include one or more protrusions, and one or more holes. For example, the first module 156 may also include a protrusion that may couple to a cavity of a module provided on an opposite side of the first module 156. Similarly, the second module 158 may also include a cavity that may couple to a protrusion of a module provided on an opposite side of the second module 158. This way, the modular phantom may be formed by coupling one module to an adjacent module. In some embodiments, the peg-and-hole attachment means may be used along with other attachment means, such as one or more support rods.

According to various embodiments, the modular phantom may also include one or more instruments (e.g. ionization chambers) for dosimetry measurement. Referring back to FIG. 1A, the modular phantom 100 may include a central through hole 104 provided at the center (along a central line) of the modular phantom 100. The plurality of through holes 102 may be provided around the central through hole 104. One or more of the through holes 102, and/or the central through hole 104 may also serve as ionization chamber holes configured to receive an instrument (e.g. an ionization chamber or a similar dosimeter) for measuring the dosimetry of the medical imaging system, which is discussed below in greater detail.

Figure 2A:
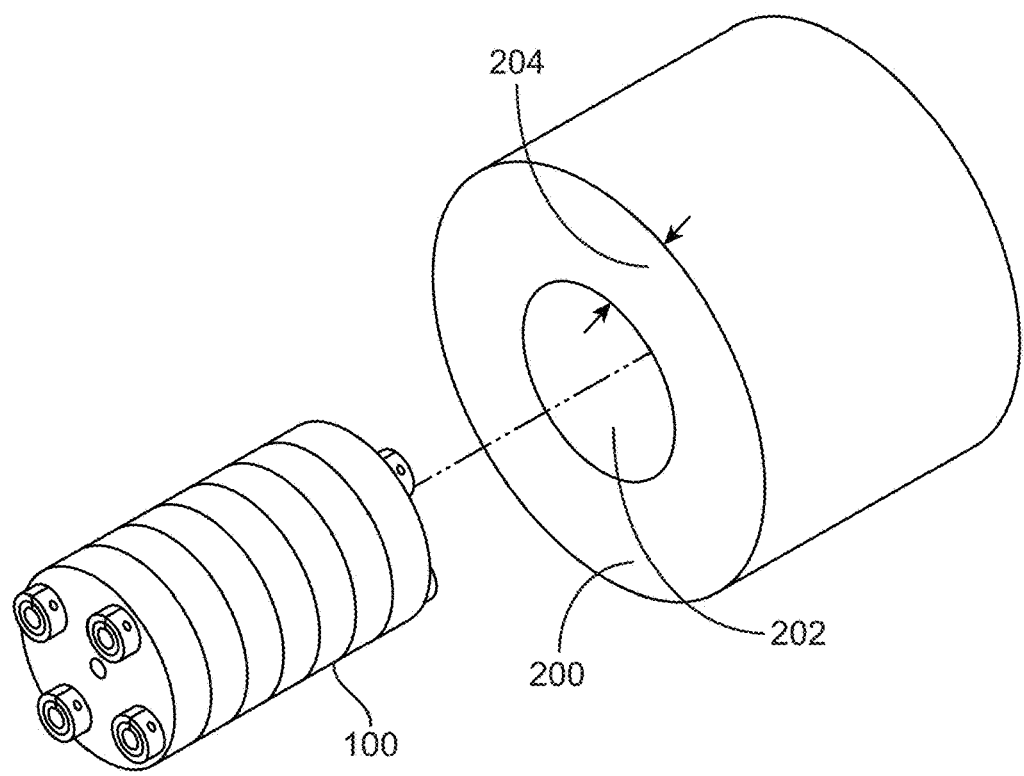
FIGS. 2A-2B illustrate an exemplary sleeve for the modular phantom in accordance with embodiments of the invention.
Figure 2B:
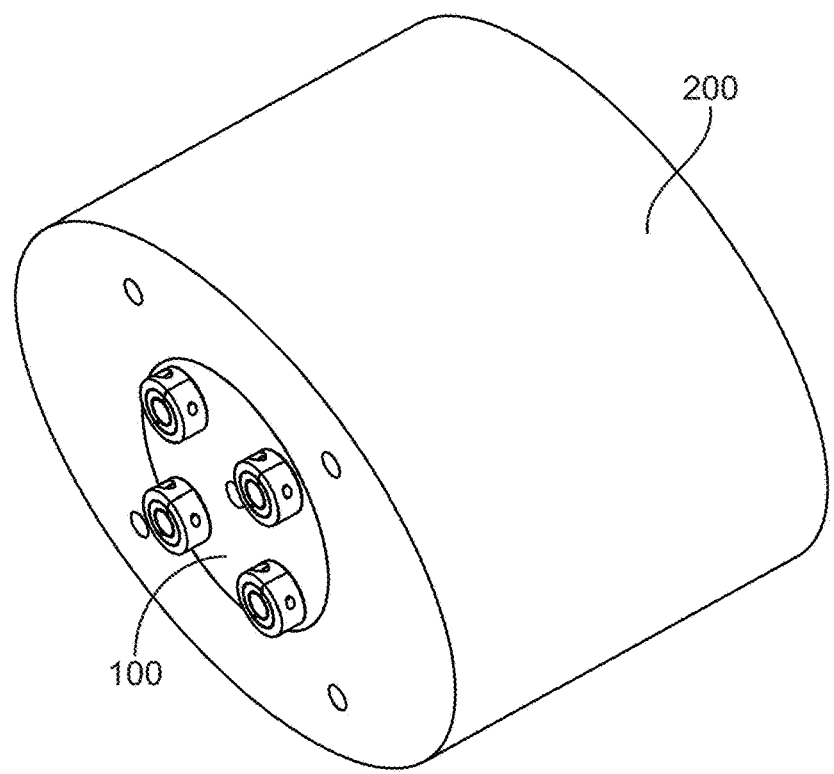

As provided above, an exemplary attachment means may include a sleeve (e.g. an annulus). FIGS. 2A-2B illustrate an exemplary sleeve 200 having a central through hole 202 for receiving one or more of the modules of the modular phantom 100 therein. The sleeve 200 may have a predetermined thickness 204 that may depend, for example, of the properties of the imaging system where the modular phantom 100 will be used. In some embodiments, the predetermined thickness 204 may depend, for example, of the properties of the imaging system that will be assessed using the modular phantom 100. According to various embodiments, the sleeve 200 may have any shape or form. For example, the sleeve 200 may be a circular sleeve (as illustrated in FIG. 2A) or elliptical (as illustrated in FIG. 2B). In some embodiments, the sleeve 200 may be a solid sleeve. The sleeve 200 may include one or more peripheral holes.

According to various embodiments, the modular phantom (as well as each module) may have any size and dimension according to the particular use of the modular phantom 100. In some embodiments, the diameter of the modular phantom 100 may be about 18 cm or less. The sleeve 200 that envelops the modular phantom 100 may increase an external diameter of the modular phantom. In some embodiments, the diameter of the sleeve 200 containing the modular phantom 100 may be a size suitable for use in connection with a CT scanner (e.g., about 32 cm). For example, for an elliptical phantom sleeve, the diameter may be 32 cm on the major axis and 24 cm on the minor axis. According to various embodiments, the sleeve 200 may be configured to keep the various modules together, while the sleeve may also be configured to increase the diameter of the phantom to a diameter larger than the diameter of the various modules.

The various phantom modules will be described next.

Figure 3C:
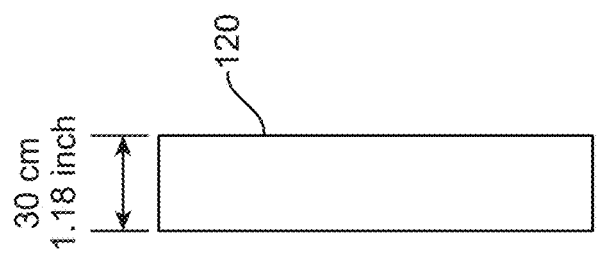
FIG. 3C illustrates a side view of a cone-beam module in accordance with embodiments of the invention.
Figure 3B:
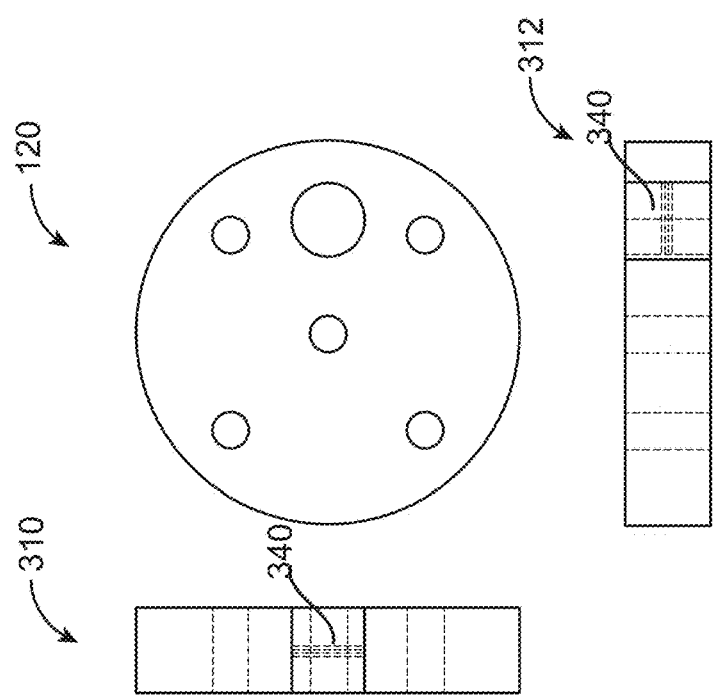
FIG. 3B illustrates a top view and corresponding cut-out views of a cone-beam module in accordance with embodiments of the invention.
Figure 3A:
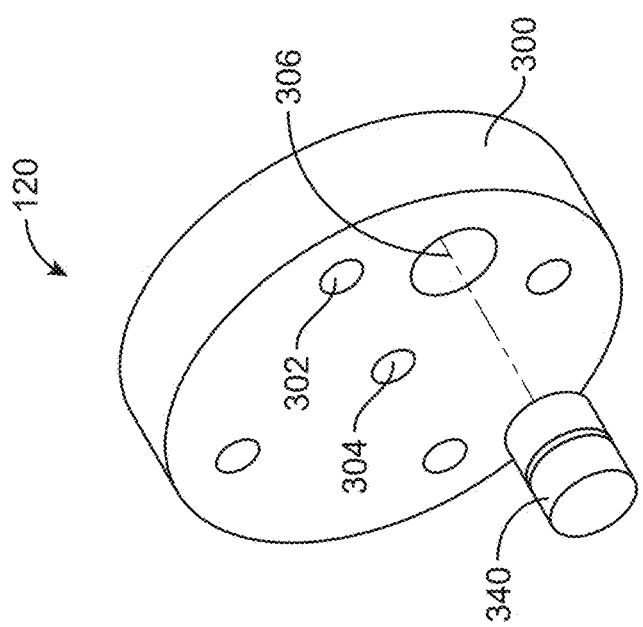
FIG. 3A illustrates a perspective view of a cone-beam module in accordance with embodiments of the invention.

FIG. 3A illustrates a perspective view of an exemplary cone-beam module 120. FIG. 3B illustrates the top view of the exemplary cone-beam module 120 and FIG. 3C illustrates a side view thereof. The cone-beam module 120 may include a body 300, a plurality of through holes 302 and a central through hole 304 provided at the center (along a central line) of the body 300. The plurality of through holes 302 may be provided around the central through hole 304 that may remain hollow or may receive an instrument therein. According to various embodiments, the through holes 302 may have a dual purpose. The plurality of through holes 302 may form pathways for the attachment means (e.g., support rods 160) and/or may receive an instrument (e.g. an ionization chamber). The cone-beam module 120 may also include a cavity 306 adapted to receive an insert 340 based on a medical imaging and dosimetry application associated with the cone-beam module 120. The cavity 306 may extend along a portion of the height (e.g. depth) of the cone-beam module 120. In some embodiments, the cavity 306 may extend along the entire height of the cone-beam module 120 and may be a through hole. The details of the insert 340 are shown in FIGS. 3G-3J. In some embodiments, the cavity 306 may have a larger diameter than the plurality of through holes 302.

The cone-beam module 120 may be used to measure a cone-beam artifact for a particular imaging system. The cone-beam artifact may refer to an error in an image acquired with the particular imaging system. The cone-beam artifact may be induced by discrepancies between the mathematical modeling and the actual physical imaging process. The presence of the cone-beam artifact in an acquired image may degrade the quality of the image to a non-diagnostic level. The cone-beam module 120 may be used to quantify an amplitude of the cone-beam artifact in a manner that is interpretable between various imaging and analysis systems.

As described below, the cone-beam module 120 may be placed at various cone angles (i.e., distance from the central axial plane containing a ray from the radiation source that is perpendicular to the detector of the imaging system) to characterize the dependence of cone-beam artifact on position in the image reconstruction. In some embodiments, the cone-beam artifact is expected to be very small/negligible in the central axial plane. The artifact may become more severe as the cone-beam module 120 is placed farther (in +/−z direction) from the central axial plane. As used herein, the x and y directions define the axial plane (e.g., the transaxial or transverse plane). The z direction marks the long direction of the modular phantom 100, as shown in FIG. 1C.

FIG. 3B illustrates cut-out views 310 and 312 of the cone-beam module 120 including the insert 340 at the cavity 306. According to the various embodiments, the cavity 306 may be provided anywhere on the body 300 of the cone-beam module 120.

FIGS. 3G-3J illustrate the details of the insert 340. According to exemplary embodiments, the insert 340 may be a solid object having a smooth surface. The insert 340 may include at least two components (e.g. two discs 348, 349) stacked along a z-direction of the cone-beam module 120. The components of the insert 340 may include a first portion 342 and a second portion 344 that sandwich a first disc 346 provided between two secondary discs 348 and 349. Thus, the insert 340 may be formed of a first background portion (e.g. the first portion 342), a first disc (e.g. secondary disc 348), a second background portion (e.g. first disc 346), a second disc (e.g. secondary disc 349), and a third background portion (e.g. the second portion 342). The thickness of the background portions may depend upon the particular use of the insert 340. A diameter of the first disc 346 may be equivalent to a diameter of the first portion 342 and the second portion 344 of the insert 340, as well as a diameter of the secondary disks 348 and 349. According to various embodiments, the body 300 and/or the insert 340 of the cone-beam module 120 may be made of acrylic, polycarbonate, Delrin, polyethylene, any member of the plastic or polyurethane, Teflon. In some embodiments, the body 300 may be made of a first material and the insert 340 may be made of a second, different, material. For example, the body 300 may be made of acrylic and the insert 340 may be made of Teflon.

Figure 3D:
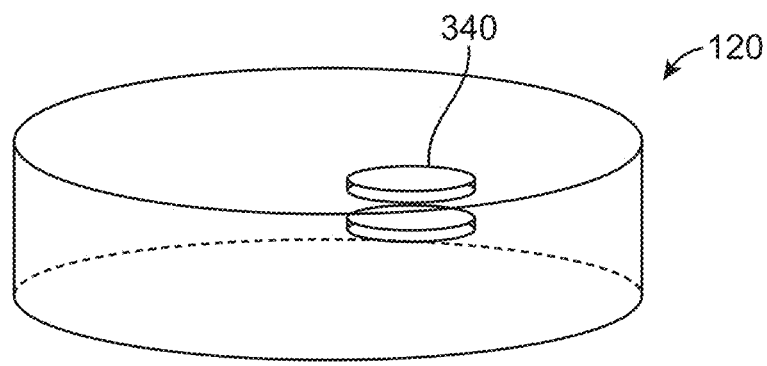
FIG. 3D illustrates an exemplary cone-beam module, excluding holes for support rods and dosimetry in accordance with embodiments of the invention.
Figure 3E:
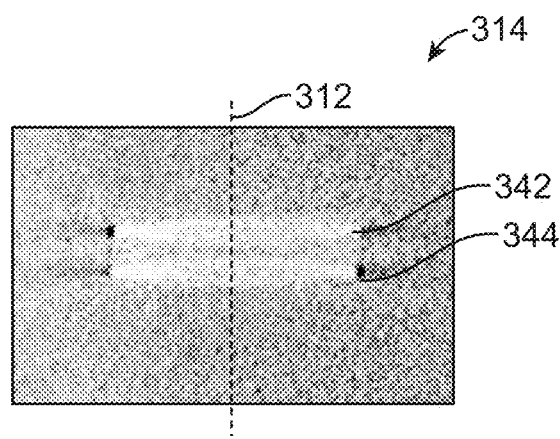
FIG. 3E illustrates an image of the cone-beam module of FIG. 3D captured in a tomographic plane (for example, a coronal or sagittal slice) perpendicular to the plane of the disks of the insert in accordance with embodiments of the invention.
Figure 3F:
FIG. 3F illustrates an exemplary profile of pixel values corresponding to the axis illustrated in FIG. 3E.
Figure 3G:
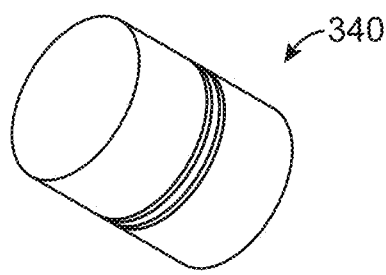
FIG. 3G illustrates a perspective view of an exemplary cone-beam module insert in accordance with embodiments of the invention.
Figure 3H:
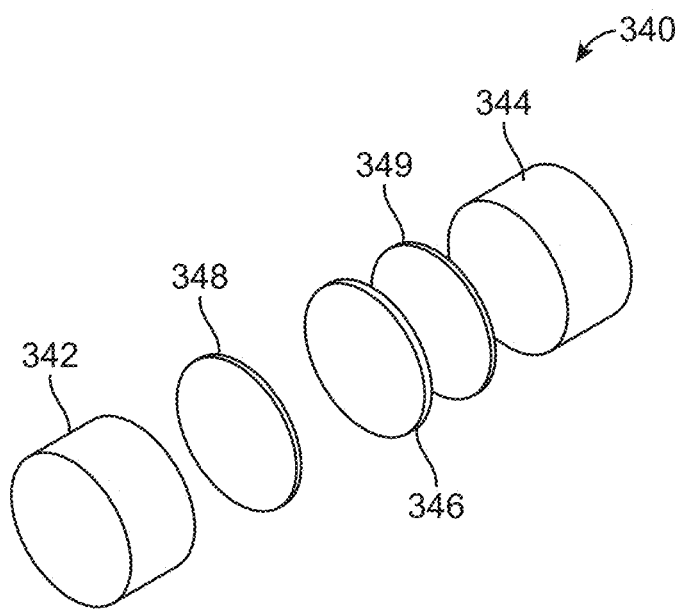
FIG. 3H illustrates a perspective view of components of an exemplary cone-beam module insert in accordance with embodiments of the invention.
Figure 3I:
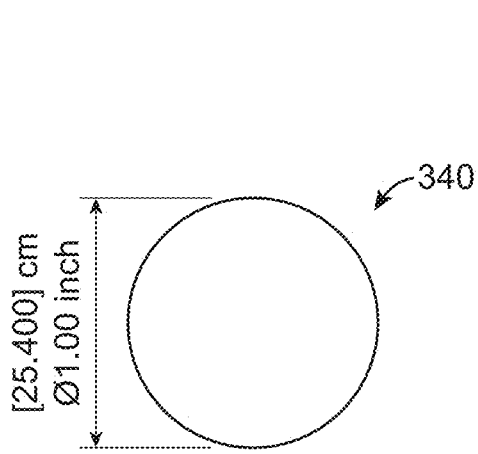
FIG. 3I illustrates a top or bottom view of an exemplary cone-beam module insert in accordance with embodiments of the invention.
Figure 3J:
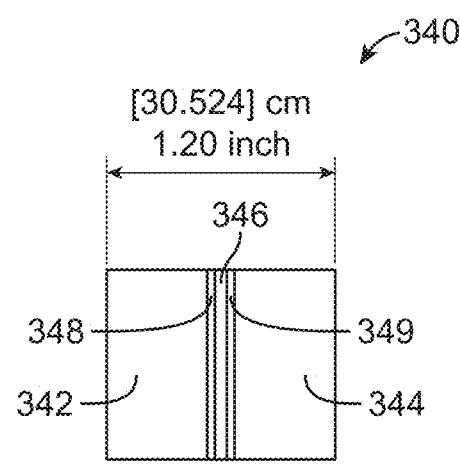
FIG. 3J illustrates a side view of an exemplary cone-beam module insert in accordance with embodiments of the invention.

As provided above, the cone-beam module 120 may be used to measure the cone-beam artifact for a particular imaging system. FIG. 3D illustrates an exemplary cone-beam module 120, excluding holes for support rods and dosimetry in accordance with embodiments of the invention. As illustrated in FIG. 3D, the insert 340 including at least two disc-shaped portions that may be inserted in the cavity 306 of the cone-beam module 120. FIG. 3E illustrates an image 314 of the cone-beam module 120 captured in a tomographic slice (for example, a coronal or sagittal slice) that is perpendicular to the plane of the two portions 342, 344 of the insert 340. One or more profiles of the image pixel values may be acquired as depicted by the axis 312. This profile may be one line of voxels, or a number of adjacent voxels may be averaged. FIG. 3F illustrates an exemplary profile 318 corresponding to the axis illustrated in FIG. 3E. The profile 318 illustrates peaks (P) 322, valley (V) 324 and background (B) 326. The cone-beam factor (U) may be defined as $$U = \frac{P-V}{P-B}$$

where U=1 if V=B (i.e., if the pixel value of the valley equals that of the background), and U=0 if V=P (i.e., if the pixel value of the valley equals that of the peak), and U has a value between 0 and 1 for values of V that are intermediate to B and P.

The cone-beam factor (U) provides a quantitative measurement of the magnitude of cone-beam artifact. The cone-beam factor (U) may represent the severity of the cone-beam artifact. The cone-beam factor may be mathematically converted to a range where U spans from 0% (no cone-beam artifact) to 100%.

Figure 4A:
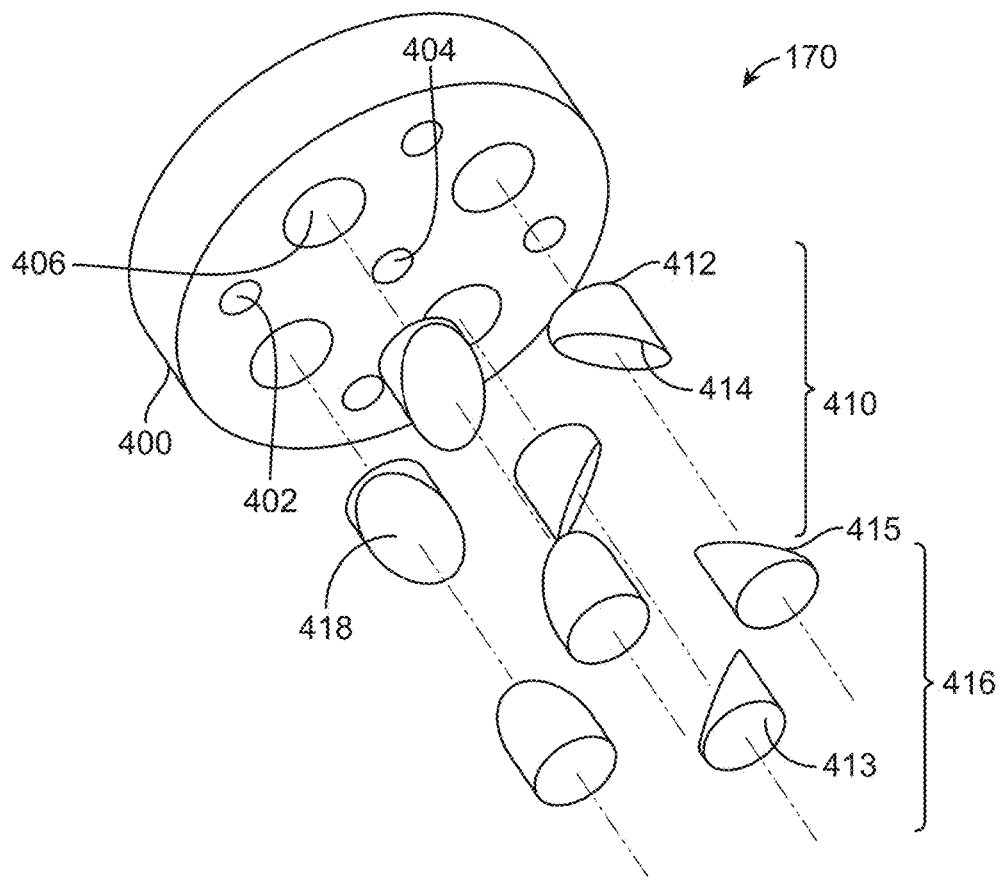
FIG. 4A illustrates exemplary angled edge module and inserts in accordance with embodiments of the invention.

Another type of module used in the modular phantom 100 may be an angled edge module 170 configured to characterize at least one of a spatial resolution or contrast properties of the imaging system. The contrast properties of the imaging system may include one or more of contrast, contrast-to-noise ratio, and the modulation transfer function (MTF) as a function of constant of the imaging system. MTF may represent the spatial frequency response of the imaging system or a component. MTF may represent the contrast at a given spatial frequency relative to low frequencies. FIG. 4A illustrates a perspective view of an exemplary angled edge module 170. The angled edge module 170 may include a body 400, a plurality of through holes 402 and a central through hole 404 provided at the center (along a central line) of the body 400. The plurality of through holes 402 may be provided around the central through hole 404. The plurality of through holes 402 form pathways. In some embodiments, attachment means (e.g., support rods) may be inserted into the pathways formed by the through holes 402 to keep the modules of the assembled modular phantom 100 in place. One or more of the through holes 402, and/or the central through hole 404 may receive an instrument (e.g., an ionization chamber) for dosimetry measurement, which is discussed below in greater detail.

According to various embodiments, the plurality of through holes 402 of the angled edge module 170 may be aligned with the through holes 302 of the cone-beam module 120. The angled edge module may also include a plurality of cavities 406. The cavity 406 may extend along a portion of the height (e.g. depth) of the angled edge module 170. In some embodiments, the cavity 306 may extend along the entire height of the angled edge module 170 and may be a through hole. In some embodiments, the cavities 406 may have a larger diameter than the plurality of through holes 402. In other embodiments, the cavities 406 may have diameters of same or comparable size as the diameters of the through holes 402. The plurality of cavities 406 may be dispersed along the surface of the angled edge module 107 in an alternating manner with the plurality of through holes 402. According to various embodiments, the angled edge module 170 may also include one or more inserts 418 provided, for example, in the central through hole 404, or in one or more of the plurality of cavities 406. The inserts 418 of various contrast to the background material, thereby allowing measurement of contrast properties (e.g. contrast, contrast-to-noise ratio, and the modulation transfer function (MTF)) of the imaging system. In some embodiments, the edges of the inserts 418 may be used to measure the edge-spread function and modulation transfer function as a measurement of spatial resolution (in the axial plane). According to some embodiments, an exemplary imaging system may exhibit contrast-dependent spatial resolution, so the ability to measure the edge-spread function for various contrast levels may be particularly useful.

The inserts 418 may include at least one angled edge or an angled surface that allows the measurement of the edge spread function in the directions x, y, and/or z of the modular phantom. The edge spread function may be considered to be the integral of the line-spread function, and may be used to compute the modulation transfer function (MTF). According to various embodiments, the edge 414 of the insert 418 of the angled edge module 170 form the basis for the edge spread measurement. From the edge 414 of the insert 418, the MTF can be measured in the x or y directions (or any angle in the xy plane). In some embodiments, the angled edge module 170 may be oriented in various directions to measure the edge spread function in x, y, or any intermediate directions in the axial plane. In some embodiments, the angled edge module 170 may be converted to a module that presents the edge spread object (e.g., the insert 418) at an angle that is not orthogonal to the axial plane. For example, placing the edge spread object at 450 to the axial plane may allow measurement of the edge spread function in the z direction.

Figures 4B, 4C, 4D:
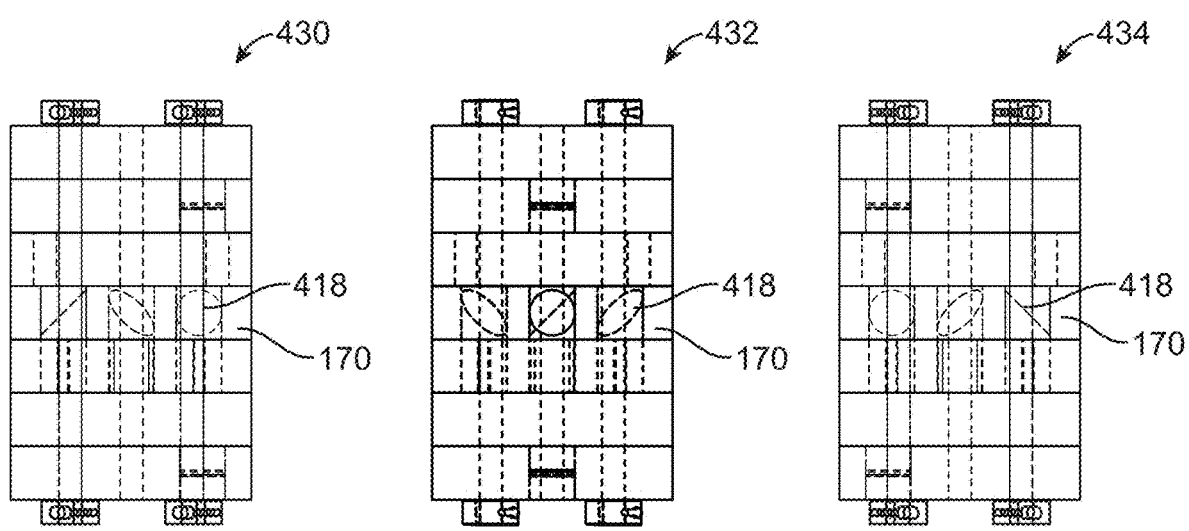
FIGS. 4B-4D illustrate cross-sectional views of an exemplary modular phantom including an angled edge module in accordance with embodiments of the invention.

FIGS. 4B-4D show cross-sections of an exemplary modular phantom including at least one angled edge module 170. The modular phantom is rotated around its central axis between each cross section 430, 432 and 434 illustrated in FIGS. 4B-4D, respectively. FIGS. 4B-4D illustrate different cross sectional views of the insert 418 provided at all four cavities 406 of the angled edge module 170.

As illustrated in FIG. 4A, the inserts 418 may have various types of angled edges 414. For example, the first set of inserts 410 may be inserted into the angled edge module 170 to have a flat edge 412 at a first end (e.g., bottom) of the angled edge module 170 and an angled edge 414 at a second end (e.g., top) of the angled edge module 170. The second set of inserts 416 may be inserted into the angled edge module 170 to have an angled edge 415 at a first end (e.g., bottom) of the angled edge module 170 and a flat edge 413 at a second end (e.g., top) of the angled edge module 170. The first set of inserts 410 and the second set of inserts 160 are shown for illustrative purposes and should not be viewed as limiting. In some embodiments, the inserts may be mixed and matched, and the set of inserts may have non-identical inserts. In some embodiments, multiple inserts may be provided in the same cavity 406. According to some embodiments, the edge 414 of the insert 418 may be flat, curved, linear or non-linear.

Figure 4E:
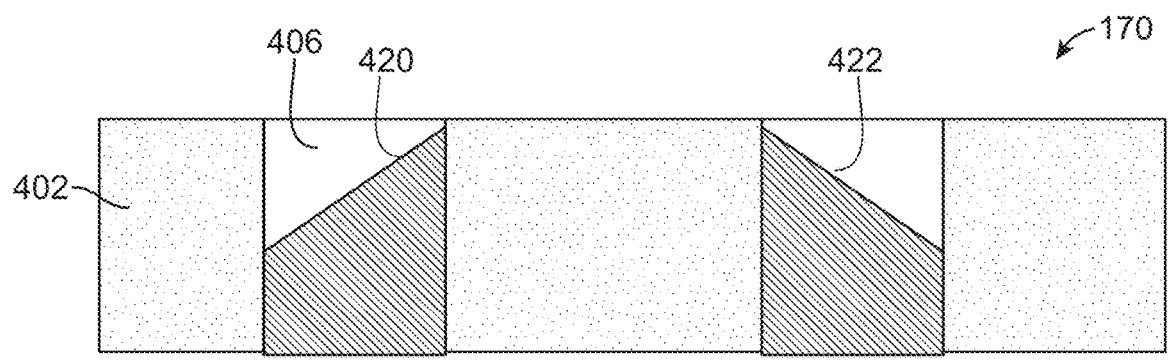
FIGS. 4E-4H illustrate exemplary angle edge modules with various types and number of inserts in accordance with embodiments of the invention.

FIGS. 4E-4H illustrate exemplary inserts 420-428 for the angled edge module 170. According to some embodiments, the angled edge module 170 may include at least two inserts 420 and 422. As illustrated in FIG. 4E, the first insert 420 and the second insert 422 may have different shapes, or may be inserted in the corresponding cavities 406 to form a desired shape. For example, the first insert 420 and the second insert 422 may be provided to be symmetrical with respect to a central axis of the angled edge module 170. The first insert 420 and the second insert 422 may be provided in the angled edge module 170 to be parallel to each other. In some embodiments, one or more inserts may be identical (i.e., may have the same shape). As illustrated in FIG. 4E, the inserts 420 and 422 have a planar surface and one or more edges that are presented at a predetermined angle (e.g., 45°).

Figure 4F:
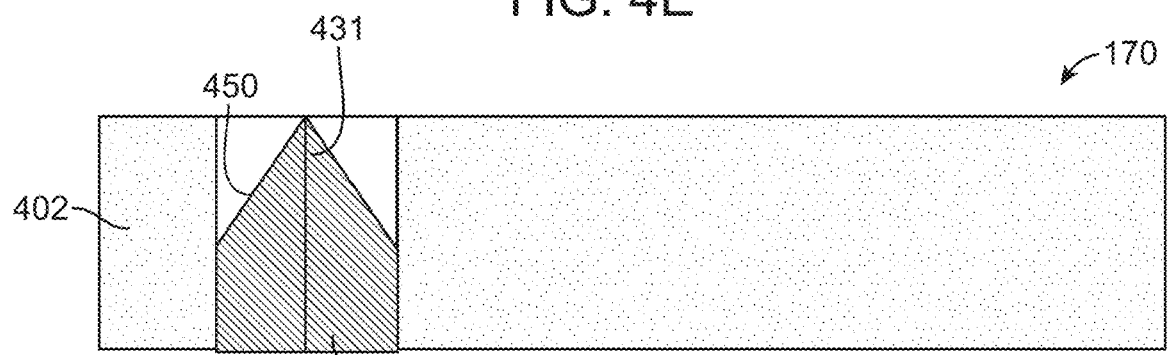

According to various embodiments, the surface of the inserts may have any shape or form. The surfaces may be flat or curved, linear or non-linear. FIG. 4F illustrates the angled edge module 170 with an exemplary insert 424 having an angled edge 450 presented at a given angle with respect to the z axis 431 but the angle normal to the angled edge 450 precesses about the z axis 431 (e.g., the insert 424 is a cone). According to various embodiments, the edge surface 450 may be flat, curved, or may have surface irregularities.

Figure 4G:
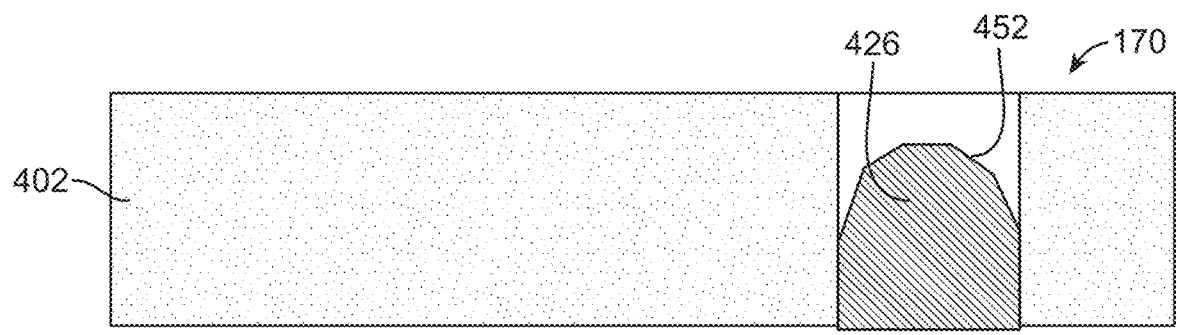

FIG. 4G illustrates an angled edge module 170 having an insert 426 with a series of angled edges 452 with different angles (i.e., the insert 426 is a polyhedron), making the insert 426 piece-wise flat but with angled edges 452 expressed in three dimensions with a multitude of different facet angles.

Figure 4H:
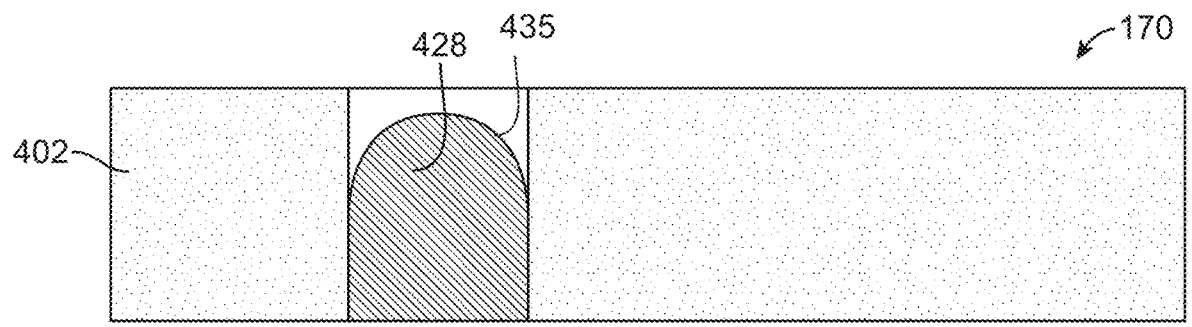

FIG. 4H illustrates an angled edge module 170 with an insert 428 having a smooth, curved surface 435 in three dimensions. According to various embodiments, the surface 435 of the insert 428 may be hemispherical, elliptical, or otherwise non-planar in cross section.

According to various embodiments, the body 400 and/or the insert(s) 418 of the angled edge module 170 may be made of acrylic, polycarbonate, Delrin, polyethylene, Teflon, various polyurethane mixtures, or any plastic presenting a relatively homogeneous material that is different from the background material. For example, the body 400 of the angled edge module 170 may be made of acrylic and the insert 418 may be made of Teflon. In some embodiments, the body 400 may be made of a first material and the insert 418 may be made of a second, different, material.

According to some embodiments, the modular phantom may include two or more angled edge modules, the insert of each of the angled edge modules may be made of a different material. For example the insert in the first angled edge module may be made of Delrin, and the insert in the second angled edge module may be made of Teflon. In some embodiments, a given angled edge module may include more than one insert, each insert made of different material. Using inserts made of different materials (as well as surface features, edge angles) may allow for measuring different properties of the MTF including characterizing the MTF at different contrast levels, which may be impacted by various reconstruction algorithms.

In some embodiments, the angled edge module 170 can be used to measure (1) the contrast (i.e., the difference in average pixel value within the insert and in the background), (2) the contrast to noise ratio (CNR), which is the contrast divided by a measure of the standard deviation in the insert and/or background, and (3) the MTF at one or more levels of contrast. For various CT or cone-beam CT systems, spatial resolution may depend on the contrast. For such systems, a "nonlinear" image reconstruction algorithm may be used. Accordingly, an angled edge module configured to measure MTF at different levels of contrast may be used connection with those CT or cone-beam CT systems where the spatial resolution depends on the contrast.

Figure 5A:
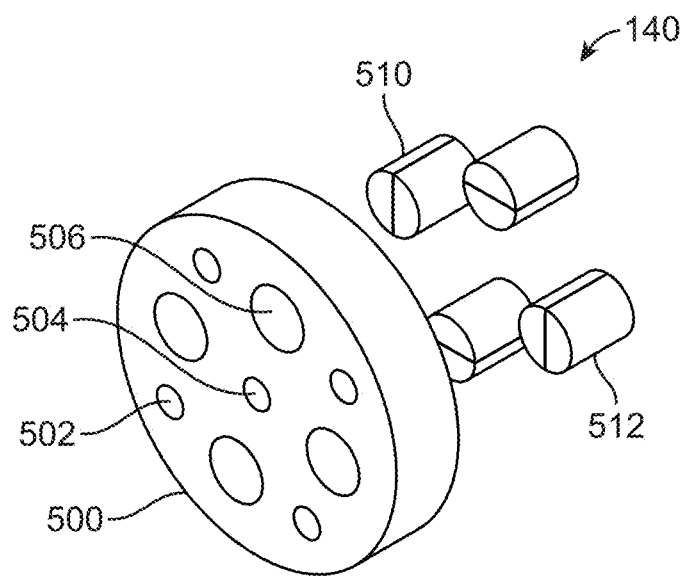
FIG. 5A illustrates a perspective view of exemplary line spread module in accordance with embodiments of the invention.
Figure 5B:
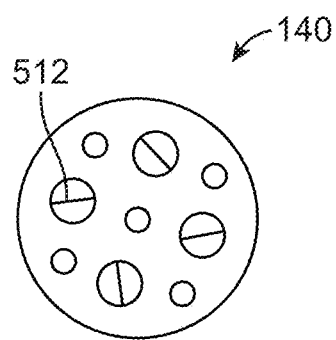
FIG. 5B illustrates a top/bottom view of a line spread module in accordance with embodiments of the invention.
Figure 5C:
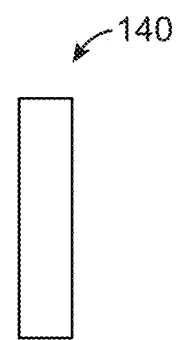
FIG. 5C illustrates a side view of a line spread module in accordance with embodiments of the invention.

Another module that may be used in connection with the modular phantom 100 may be a line spread module 140. FIG. 5A illustrates a perspective view of an exemplary line spread module 140. FIG. 5B illustrates the top/bottom view of the exemplary line spread module 140 and FIG. 5C illustrates a side view thereof.

According to various embodiments, the line spread module 140 may be used to measure line-spread function of the imaging system. The line-spread function may be analyzed in terms of the modulation transfer function for characterization of spatial resolution of the imaging system. In some embodiments, the line spread module 140 may be oriented in various directions to measure the line-spread function in the x or y direction, or intermediate directions in the axial plane. In some embodiments, the line spread module 140 may be converted to a module that presents the line spread object at an angle that is not orthogonal to the axial plane. For example, placing the line spread object at 450 to the axial plane may allow measurement of the line-spread function in the z direction.

In some embodiments, the angled edge module 170 may be designed to measure the modulation transfer function (MTF) in the x, y, z, or any intermediate directions, while the line spread module 140 may be designed to measure the MTF in the x, or y directions, or in any direction in the (x, y) plane.

Referring to FIG. 5A, the line spread module 140 may include a body 500, a plurality of through holes 502 and a central through hole 504 formed in the body 500, at the center (along a central line) of the line spread module 140. The plurality of through holes 502 may be provided around the central through hole 504. According to various embodiments, the central through hole 504 may remain hollow or may receive an instrument. In some embodiments, the plurality of through holes 502 form pathways for the attachment means (e.g., support rods 160) to keep the modules of the assembled modular phantom 100 in place. In some embodiments, the plurality of through holes 502 of the line spread module 140 may be aligned with the through holes 302 of the cone-beam module 120.

The line spread module 140 may also include a plurality of cavities 506 with a larger diameter than the plurality of through holes 504. The plurality of cavities 506 may be dispersed along the surface of the line spread module 140 in an alternating manner with the plurality of through holes 504. The cavity 506 may extend along a portion of the height (e.g. depth) of the line spread module 140. In some embodiments, the cavity 506 may extend along the entire height of the line spread module 140 and may be a through hole. According to various embodiments, the line spread module 140 may also include a plurality of 510 inserts provided in one or more of the cavities 506. Each insert 510 may be include a slit 512 that extends along a central line of the insert 510. As shown in FIG. 5B, according to various embodiments, the slits 512 of the plurality of inserts 510 may not be aligned on the surface of the line spread module 140. According to various embodiments, the slit 512 is provided to form a contrast from the surrounding insert 510. In some embodiments, instead of (or in addition to) a slit, the inserts 510 may include a thin sheet or film of material that results in a contrast from the surrounding plug.

Figure 5D:
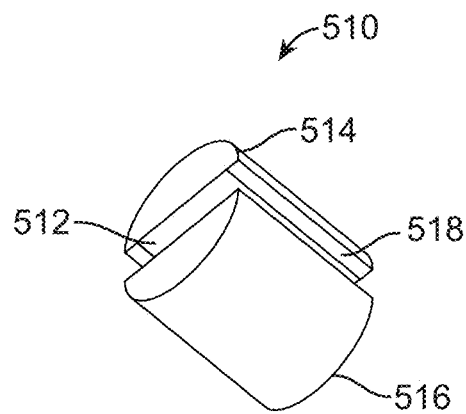
FIGS. 5D-5E illustrate exemplary insert components for a line spread module in accordance with embodiments of the invention.
Figure 5E:
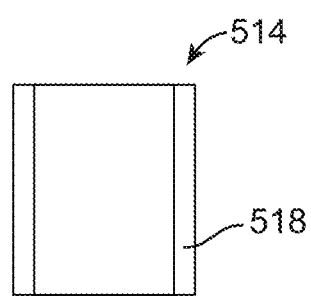

The details of the insert 510 are shown in FIGS. 5D-5E. The insert 510 may include a first component 514 and a second component 516 separated by the slit 512 extending along a central line of the insert 510. The first component 514 and the second component 516 may be stacked along a x-direction of the line spread module 140. As illustrated in FIG. 5E, at least one of the first component 514 and the second component 516 may include surface features such as protrusions 518 along the surface of the component. The protrusion 518 may form the slit 512 between the first component 514 and the second component 516.

Figure 6A:
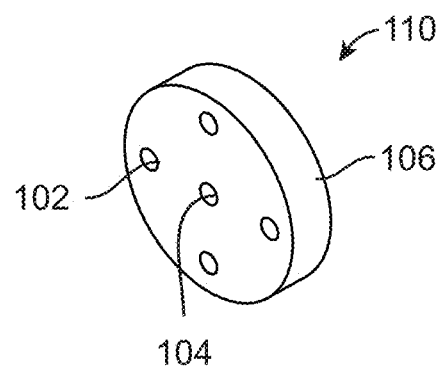
FIG. 6A illustrates a perspective view exemplary uniform module in accordance with embodiments of the invention.
Figure 6B:
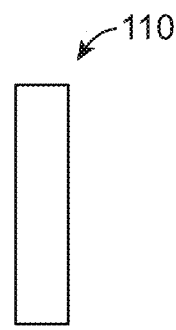
FIG. 6B illustrates a side view of a uniform module in accordance with embodiments of the invention.

Another type of module that may be used in connection with the modular phantom 100 described herein may be a homogenous module (e.g., a uniform module) 110. FIG. 6A illustrates a perspective view of an exemplary uniform module 110. FIG. 6B illustrates a side view of uniform module 110. The uniform module 110 may be used to measure the uniformity, noise, and/or noise-power spectrum (each of which is defined above) associated with the medical imaging device. In some embodiments, the uniform module 110 may be used for dosimetry assessment of the medical imaging device. For example, the instrument for assessing the dosimetry (e.g. a dosimetry meter or the dosimetry ion chamber) may be provided within through holes of the uniform module 110.

The uniform module 110 may include a body 106, a plurality of through holes 102 and a central through hole 104 formed on the body 106. The central through hole 104 may be provided at the center (along a central line) of the uniform module 110. The plurality of through holes 102 are provided around the central through hole 104. In some embodiments, the central through hole 104 may remain hollow or may receive an instrument therein. In some embodiments, the plurality of through holes 102 may be provided uniformly around the central through hole 104. The plurality of through holes 102 form pathways for the attachment means (e.g., support rods 160) to keep the modules of the assembled modular phantom 100 in place. The plurality of through holes 102 of the uniform module 110 may be aligned with the through holes 202 of the cone-beam module 120, the through holes 302 of the angled edge module 170, and the through holes 402 of the line spread module 140.

In some embodiments, a radiation exposure meter may be inserted in one of the through holes 102 and the central through hole 104 of the modular phantom 100. The uniform module 110 may be suitable for providing the radiation exposure meter as the uniform module 100 provides a non-perturbed medium for x-rays to reach the through holes 102 or the central through hole 104.

Order of the Modules in an Exemplary Assembled Phantom

A given modular phantom may include one or more modules arranged in a predetermined order that depends, in part, on characteristics of the measurements that will be made using the phantom, geometry (e.g., focal point) and properties (e.g., cone angle) of the scanner, object (e.g., body part) that is being imaged, the materials that is used for the modules, etc. The order of the modules within the phantom may also depend on the particular use of the phantom. For example, a phantom for a dental CT scanner may have modules arranged in an order that is different than a phantom for a breast CT scanner.

According to an exemplary embodiment, the phantom may include one cone-beam module placed along the central ray of a CT scanner. Other modules (including one or more of the cone-beam module, the angled edge module, the line spread module, the uniform module, and/or other module(s)) may be placed at a maximum cone angle available for a specific cone-beam CT system.

It may also be necessary to include more than one of the same module in the modular phantom depending on the desired measurements to be performed using the modular phantom. For example, a first cone-beam module may be provided along a central axial plane of the modular phantom where the cone angle is zero, and a second cone-beam module may be provided at a predetermined distance (e.g., greater than 1 cm) of the central axial plane of the modular phantom where the cone angle is not zero.

Placement of modules at a particular cone angle may be important in accurately characterizing a particular aspect of imaging performance and/or examining the dependence of a particular performance characteristic on position in the image.

For example, the cone-beam module may be placed at various cone angles to examine the dependence of the cone-beam artifact on position in the image. Typically, the cone-beam artifact increases with cone angle. Similarly, the dependence of uniformity and noise on position in the image may be investigated by positioning the uniform module at various cone angles. Similarly, the dependence of spatial resolution on position in the image may be investigated by placing the line spread module and/or the angled edge module at various cone angles. The angled edge module (angled edge or curved surface allowing measurement of ESF in the x or y or z directions) may be placed at various cone angles to characterize the dependence of spatial resolution on position in the image. Similarly, the angled edge module may be placed at various cone angles to measure the dependence of contrast and/or CNR on position in the image.

According to another exemplary embodiment, the phantom may include a line spread module aligned with the central ray of the CT scanner to optimize the evaluation of spatial resolution in the (x, y) plane of the imaging system.

According to an exemplary embodiment, the phantom may include at least one line spread module at a predetermined distance from the central ray of the CT scanner, to estimate the spatial resolution in the (x, y) plane of a practical area which would correspond to patient anatomy where there is a finite (i.e., non-zero) cone-beam angle.

According to an exemplary embodiment, the phantom may include an angled edge module at or near the central ray of the scanner to evaluate the contrast and gray scale consistency of the scanner at this optimal location in the field of view.

According to an exemplary embodiment, the phantom may include one or more of angled edge modules placed away from the central ray of the scanner where the cone angle is greater than zero degrees. The phantom may be used to evaluate how the gray scale performance of the scanner is impacted by the non-zero cone angle. This type of phantom (s) could be placed at multiple cone angles using multiple CT acquisitions, to evaluate a comprehensive measurement of gray scale performance as a function of cone angle.

According to an exemplary embodiment, the phantom may include a uniform module at the central ray of the scanner where the cone angle approaches zero degrees. This type of phantom may be used to evaluate image uniformity at this location in the scanner.

According to an exemplary embodiment, the phantom may include a uniform module located at increasing distances from the central ray of the scanner to evaluate image uniformity as a function of location (i.e., cone angle) in the scanner.

Figure 7A:
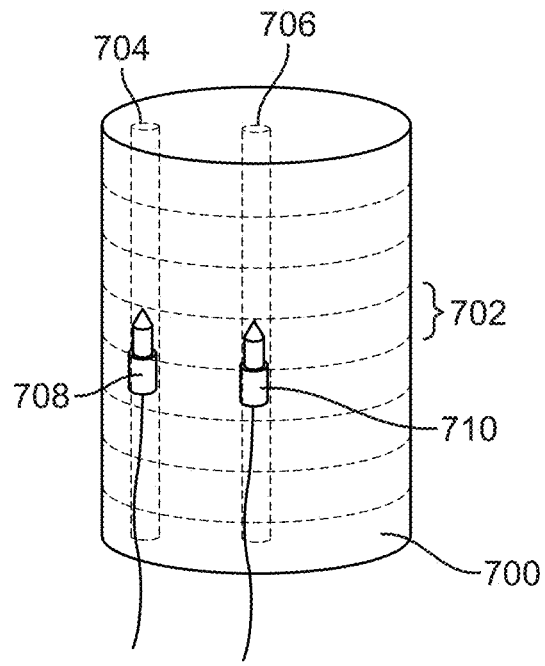
FIG. 7A illustrates an exemplary phantom with one or more radiation measurement instruments inserted in the through-holes in accordance with embodiments of the invention.

Referring now to FIG. 7A, an exemplary phantom is illustrated with one or more radiation measurement instruments inserted in long holes. The phantom 700 may include a uniform module 702 positioned near the central ray of the scanner. The phantom may also include one or more instruments such as a first instrument 708 inserted into a first cavity 704 and a second instrument 710 inserted into a second cavity 706 to measure radiation levels at, for example, the uniform module 702 level. According to various embodiments, the instruments 708, 710 may be placed at other module-levels in the phantom 700.

The instruments 708, 710 may include an air ionization chamber or similar electronic dosimeter. The instruments may similarly include other forms of dosimeter, such as thermoluminescent dosimeters or radiosensitive film (such as gafchromic film). The instrument(s) may be placed (serially using multiple CT scans) in any of the cavities illustrated in FIG. 7A, including the second (e.g., central cavity) 706 and the cavities (e.g., the first cavity 704) along the periphery of the phantom 700.

According to some embodiments, the instruments 708, 710 may communicate with a computing device via a wired or wireless connection. The instruments 708, 710 may transmit the data associated with the measurements to the computing device. The computing device may analyze the received data, and output the data to a user. In some embodiments, the instruments 708, 710 may include a built-in memory for storing data (e.g. the result of the measurements). The data may be retrieved or read from the memory of the instruments 708, 710 after removing the instruments 708, 710 from the modular phantom 700. Yet in other embodiments, the instruments 708, 710 may include a display screen for displaying the result of the measurements.

In cone-beam CT dosimetry, the instrument (e.g., the ionization chamber) may be placed within one or more of the through holes in place of the support rods. The through hole containing the instrument may be the center through hole and/or one or more of the peripheral through holes. In some embodiments, the peripheral through holes may be configured to receive the attachment means (e.g., the support rods). One or more of the peripheral holes may also be configured to accept an instrument (e.g., ionization chamber). In some embodiments, it may be desired to do a dose measurement at all through holes (i.e., the center through hole and all peripheral through holes). In other embodiments, it may be desired to do a dose measurement at a subset of the through holes. Such dose measurements may be made with the instrument positioned in the through hole, at the center module (e.g., halfway between the top and bottom of the phantom stack). In some embodiments, it may be desirable to obtain the dose measurement as a function of z. This may be achieved by pulling the ionization chamber from the center toward one end or the other end of the modular phantom.

Imaging System

Figure 7B:
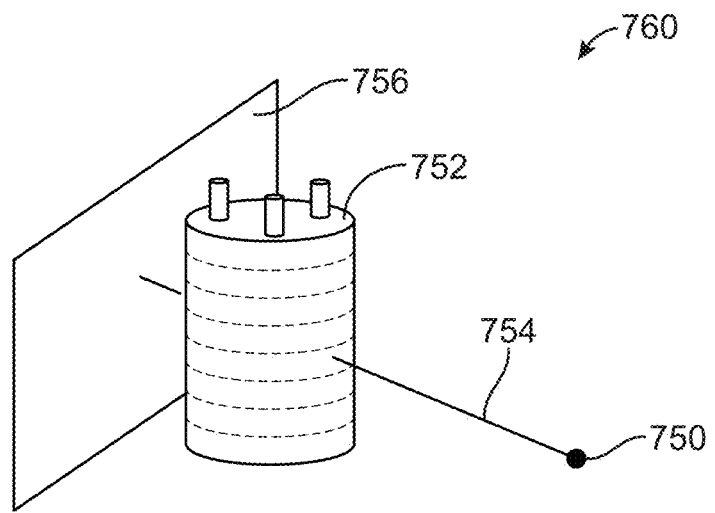
FIGS. 7B-7C illustrate an exemplary phantom aligned with a medical imaging system in accordance with embodiments of the invention.
Figure 7C:
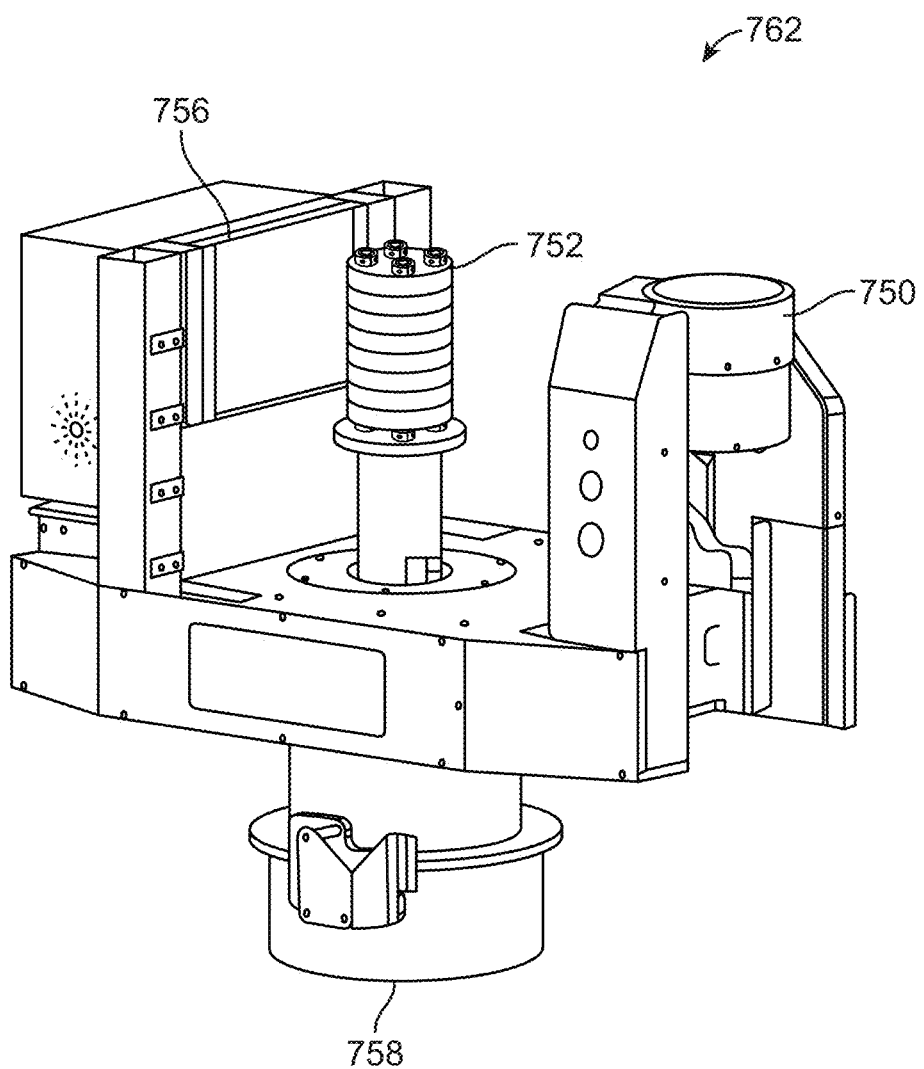

The phantom including a plurality of modules may be imaged by a cone-beam CT scanner. An exemplary medical imaging system according to embodiments is illustrated in FIGS. 7B-7C. The medical imaging system 760, 762 may include a scanner that has a radiation source 750 emitting radiation (e.g., an x-ray source emitting x-rays), a detector 756 and a target object 752 being imaged (e.g., body part or the modular phantom) placed between the radiation source 750 and the detector 756. The central ray 754 is a line emitted from the radiation source 750 and generally striking detector 756 normally with respect to the plane of the detector 756. The radiation source 750 may emit the radiation (e.g., x-rays), and the detector 756 captures the radiation (e.g., the −x-rays) that traveled through the target object 752 (e.g., the modular phantom).

As illustrated in FIG. 7C, the modular phantom 752 may be aligned with an axis of rotation 758 of the medical imaging system 762. Accordingly, the modular phantom 752 may rotate with respect to the detector 756 and the radiation source 750 during the imaging function. Image volume data of the target object 752 is captured at the detector 756. The image volume data set that is produced by that medical imaging system 760 may be gathered and evaluated using algorithms to quantify several performance parameters of the medical imaging system 760 including the magnitude of the cone-beam artifact (using the cone-beam module), the modulation transfer function (MTF) (using the angled edge module), spatial resolution (using the line spread module), contrast to noise (using the angled edge module), and gray scale uniformity or homogeneity (using the uniform module).

Figure 8:
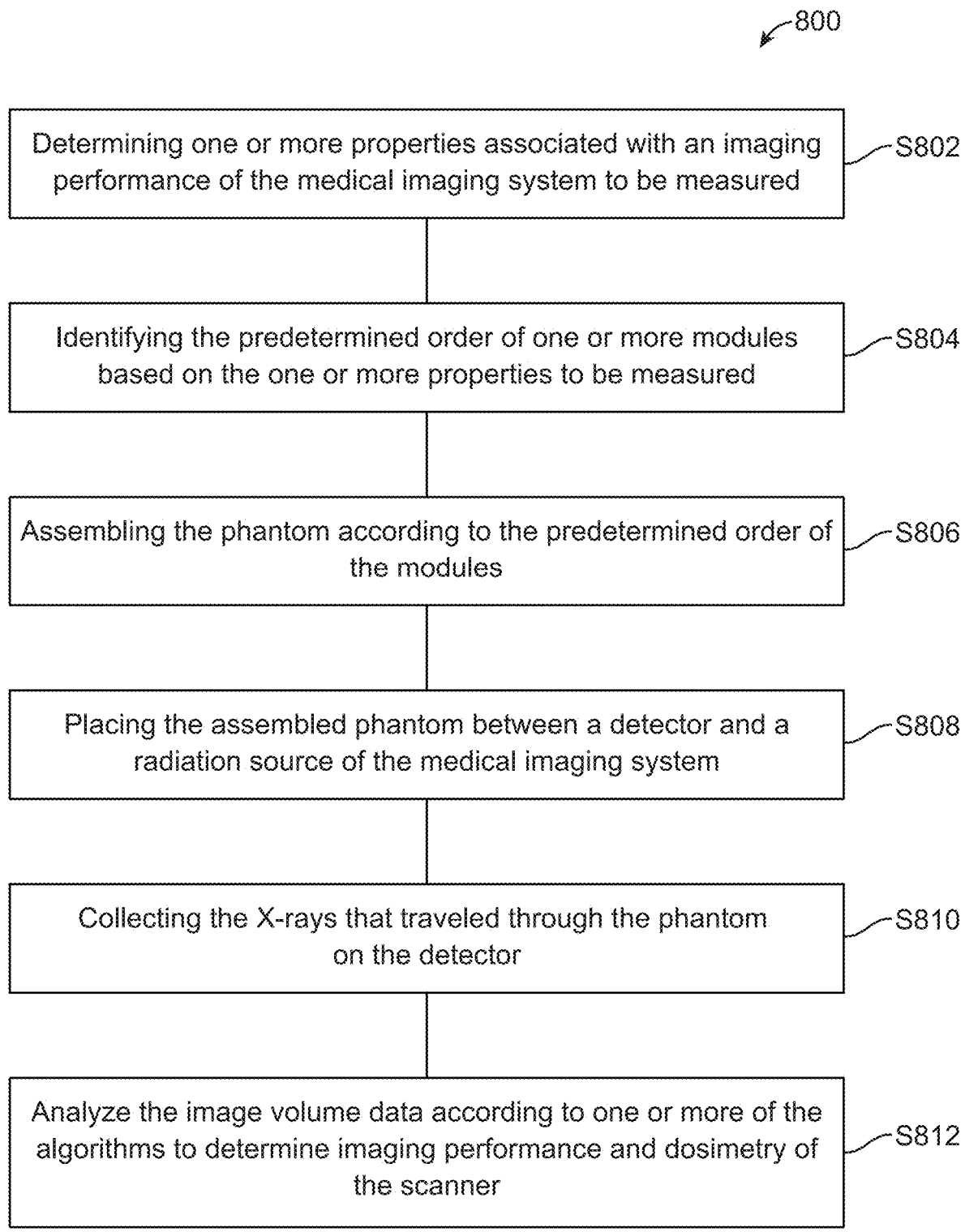
FIG. 8 illustrates a flowchart of steps for measuring the imaging performance and dosimetry of the medical imaging system in accordance with embodiments of the invention.

FIG. 8 illustrates an exemplary flowchart 800 of steps that are performed in measuring the imaging performance and dosimetry of the medical imaging system illustrated in FIG. 7B or 7C.

At step S802, one or more properties associated with an imaging performance of the medical imaging system to be measured are determined. The properties include one or more of a spatial resolution, an image uniformity, an image noise, a contrast to noise ratio, or a cone-beam artifact associated with the medical imaging system. The step may also include determining the plurality of modules that will be incorporated in the modular phantom. The plurality of modules may include one or more of a cone-beam module, a line spread module, an angled edge module, and a uniform module.

At step S804, a predetermined order of the plurality of phantoms is identified based on the one or more properties to be measured. The predetermined order may be changed as necessary, modules may be moved up and down, modules may be removed, or additional modules may be added as desired. The types of the modules to be included in the phantom and the order of the modules may also be determined based on the type of scanner (e.g., dental imaging, breast imaging, etc.) in addition to the characteristics of the scanner that needs to be determined/measured.

At step S806, the phantom may be assembled to include the plurality of modules in the predetermined order.

At step S808, the assembled modular phantom may be placed between a detector and a radiation source of the medical imaging system. For example, at least one of the plurality of modules may be aligned with a central ray of the medical imaging system. The medical imaging system (e.g., a CT scanner) may be operated such that the source of the radiation source of the medical imaging system emits radiation (e.g., X-rays) through the modular phantom.

At S810, the detector may collect/capture the X-rays that traveled through the phantom that, when acquired as a sequence of images over an angular coverage, are used to reconstruct an image volume data set. Thus, image volume data of the phantom may be produced when the data acquired by the detector are reconstructed.

At S812, the image volume data captured on the detector may be analyzed according to one or more of the algorithms to determine imaging performance and dosimetry of the scanner. For example, the image volume data may be analyzed to measure the one or more properties associated with the imaging performance of the medical imaging system and the dosimetry of the medical imaging system.

The measurement of the imaging performance and the dosimetry may be made concurrently or subsequently to each other. According to various embodiments, measurement of the imaging performance and the dosimetry may be made using the same technique factors. Thus, in some embodiments, multiple measurements may be performed using the same modular phantom.

The results of the analysis may be used to assess properties of the CT scanner and, if necessary, to calibrate the CT scanner.

According to various embodiments, the modular phantom may be used to compare multiple medical imaging systems (e.g., CT scanners). For example, an exemplary phantom including a predetermined set of modules assembled according to a predetermined order may be aligned with a first medical imaging system. Imaging performance and dosimetry of the first medical imaging system may be determined as discussed above in connection with FIG. 9. Thereafter, the same exemplary phantom may be aligned with a second medical imaging system. Imaging performance and dosimetry of the second medical imaging system may be determined as discussed above in connection with FIG. 9. The imaging performance and dosimetry of the two medical imaging systems may be compared to compare and/or calibrate the two medical imaging systems.

The imaging system may include a computer apparatus (e.g., a server computer) including one or more processors and a memory storing instructions to execute the algorithms. The computer apparatus may be coupled using wire or wirelessly to the CT scanner. For example, the computer apparatus may be coupled to the detector of the scanner to receive image data from the detector. An image volume data set is produced through reconstruction of two or more projection images. In some embodiments, the computer apparatus may also be coupled to the source so as to control (e.g., activate and deactivate) the source.

Figure 9:
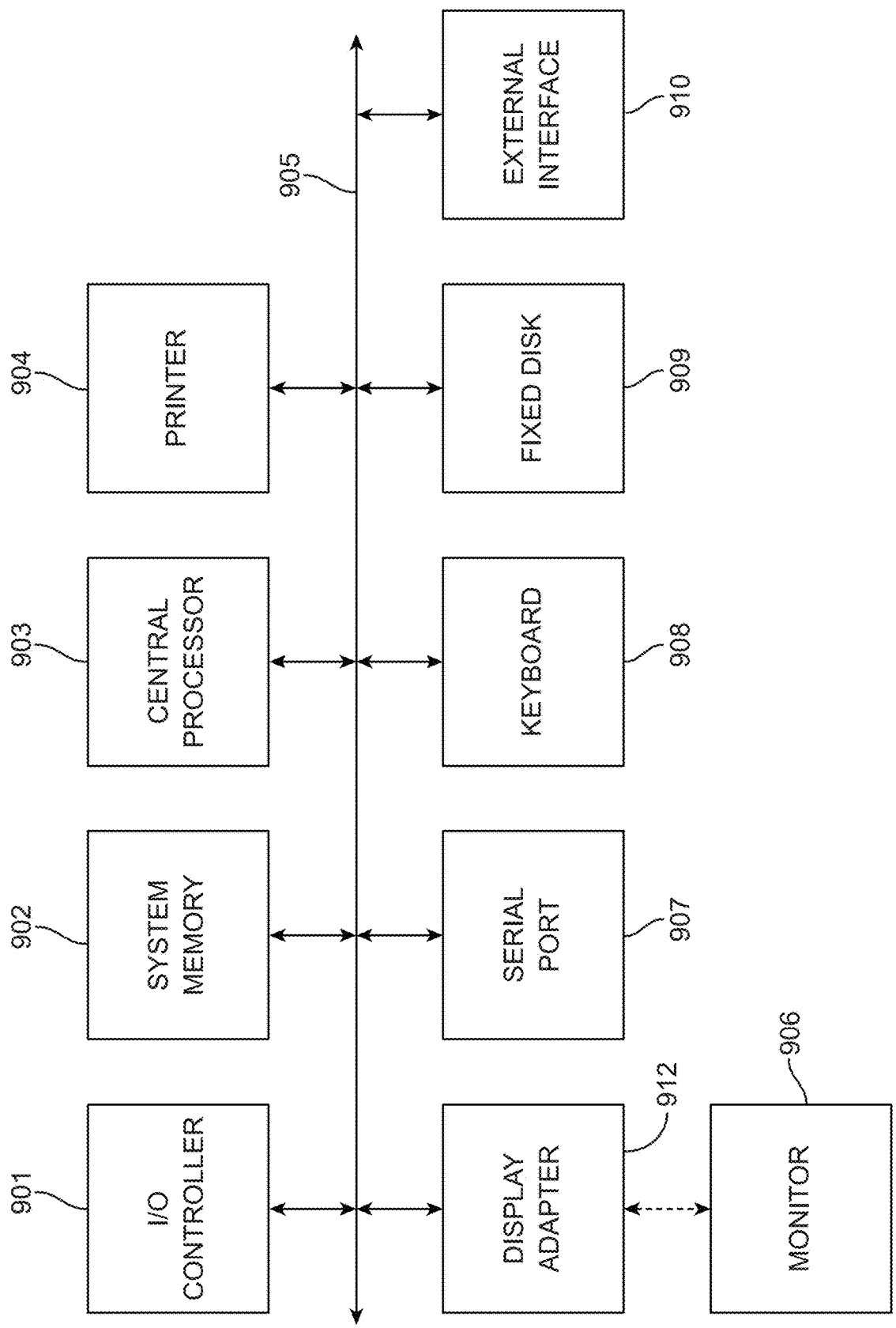
FIG. 9 illustrates shows an exemplary computer system, in accordance with embodiments of the present invention

A portion of the subsystems or components of an exemplary computer apparatus are shown in FIG. 9. The subsystems shown in FIG. 9 are interconnected via a system bus 905. The subsystems such as a printer 904, keyboard 905, fixed disk 909 (or other memory comprising computer-readable media), monitor 906, which is coupled to a display adapter 912, and others are shown. Peripherals and input/output (I/O) devices, which couple to I/O controller 901, can be connected to the computer system by any number of means known in the art, such as serial port 907. For example, serial port 907 or external interface 910 can be used to connect the computer apparatus to a wide area network such as the Internet, a mouse input device, or a scanner. The interconnection via system bus allows the central processor 903 to communicate with each subsystem and to control the execution of instructions from system memory 902 or the fixed disk 909, as well as the exchange of information between subsystems. The system memory 902 and/or the fixed disk 909 may embody computer-readable medium. The computer system described herein is then used to perform analysis of the images produced of the phantom by the cone-beam CT system.

Assessment Algorithm(s)

According to various embodiments, the algorithms may include execution on a parallel processor, such as a graphics processing unit (GPU), for determining image performance metrics using algorithms.

According to various embodiments, the algorithm for determination of spatial resolution could be designed to characterize the edge spread function (ESF) using the angled edge module (the edge of ta multi-faceted or curved surface of the angled edge module) or line-spread function (LSF) using the line spread module. The algorithm may then compute the Modulation Transfer Function from the LSF data, as well as the full width at half maximum (FWHM) of the LSF.

An embodiment of the algorithm operates on the images of the cone-beam module to estimate the contrast of the central region relative to the images of the two disks that are included in the cone-beam module. The relative contrast identified using the cone-beam modules enables to quantify the cone beam artifact for the imaging system.

Another embodiment of the algorithm operates on image data corresponding to the uniform module, and assesses a profile across this region which averages a line of image data encompassing from 1 pixel wide up to 100 pixels wide. The algorithm is designed to avoid the air holes in the phantom module.

Another embodiment of the algorithm computes the average gray scale near the center of the uniform phantom avoiding the air hole in a circular or square (or other appropriate shape) region of interest (ROI, ROIc for the central ROI) and also computes the average gray scale in one or more ROIs near the periphery of the phantom—and the peripheral ROI data is averaged (ROIp), and compared to the mean gray scale near the phantom center. The uniformity of the scanner can be quantified using metrics such as ROIc-ROIp and other simple mathematical combinations of these metrics.

Measurements of Dose Metrics and Image Performance Metrics

Phantoms according to various embodiments discussed herein may measure the imaging performance and the dosimetry of a medical imaging system (e.g., a CT scanner) using the same technique factors of the medical imaging system. The technique factors may include one or more of a tube potential, a tube current, a time of exposure, and a system geometry (e.g., a field of view (FOV) of the imaging system, a source-axis-distance (SAD) of the imaging system, a source-detector-distance (SDD), and an extent of the source-detector orbit) of the medical imaging system.

The phantoms may measure the air ionization levels (such as air kinetic energy released per unit mass (i.e., air kerma) or exposure) in the central and peripheral through-holes of the modules, and combine the air ionization levels to calculate $Ko = a \times Kc + (1-a) Kp$, where Ko is a dose related metric, Kc is the air kerma at the center hold, Kp is the air kerma averaged across one or more peripheral holes, and a is a number between 0.01 and 0.99.

An important metric determined by the phantom user (and the algorithm described herein) is to assess the imaging performance (e.g., noise, noise variance, or noise power spectrum) in the uniform module (or uniform areas of the other modules) when the dose metric Ko was measured from the same cone-beam CT scan. The dose can also be measured using the same technique factors for the medical imaging device with the dose metric (Kp) in one or more peripheral through holes of the modular phantom.

Embodiments provide a number of advantages over prior systems. Embodiments provide new and unique modules (e.g. the cone-beam module, the edge spread module, the line spread module) that, when incorporated in a modular phantom, measure imaging performance and the dosimetry of the imaging system using the same technique factors. Moreover, embodiments provide phantoms that perform a range of imaging performance measurements. The phantoms described herein are configurable in a manner suitable to a broad range of cone-beam CT scanner configurations. In addition, the phantoms described herein are consistent with emerging standards for physical measurements for cone-beam CT accreditation in a number of ways, including configurable overall dimensions (diameter and length) with use of a sleeve. Embodiments further enable calibration of the medical imaging devices, as described above.

Specific details regarding some of the above-described aspects are provided above. The specific details of the specific aspects may be combined in any suitable manner without departing from the spirit and scope of embodiments of the invention.

Storage media and computer readable media for containing code, or portions of code, may include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, data signals, data transmissions, or any other medium which may be used to store or transmit the desired information and which may be accessed by the computer. Based on the disclosure and teachings provided herein, a person of ordinary skill in the art may appreciate other ways and/or methods to implement the various embodiments.

It may be understood that the present invention as described above may be implemented in the form of control logic using computer software in a modular or integrated manner. Based on the disclosure and teachings provided herein, a person of ordinary skill in the art may know and appreciate other ways and/or methods to implement the present invention using hardware and a combination of hardware and software.

Any of the software components or functions described in this application, may be implemented as software code to be executed by one or more processors and or co-processors using any suitable computer language such as, for example, Java, C++ or Perl using, for example, conventional or object-oriented techniques. The software code may be stored as a series of instructions, or commands on a computer readable medium, such as a random-access memory (RAM), a read only memory (ROM), a magnetic medium such as a hard-drive or a floppy disk, a solid state hard drive, or an optical medium such as a CD-ROM. Any such computer readable medium may reside on or within a single computational apparatus, and may be present on or within different computational apparatuses within a system or network. The use of web-based software for phantom image analysis is also explicitly included in this description.

The above description is illustrative and is not restrictive. Many variations of the invention may become apparent to those skilled in the art upon review of the disclosure. The scope of the invention may, therefore, be determined not with reference to the above description, but instead may be determined with reference to the pending claims along with their full scope or equivalents.

One or more features from any embodiment may be combined with one or more features of any other embodiment without departing from the scope of the invention.

A recitation of "a", "an" or "the" is intended to mean "one or more" unless specifically indicated to the contrary.

What is claimed is:

1. A modular phantom for medical imaging comprising:
   one or more modules ordered according to a predetermined order, the one or more modules including at least one of a cone-beam module configured to measure a cone-beam artifact for a medical imaging system, an angled edge module configured to measure at least one of a spatial resolution or contrast properties of the medical imaging system, or a line spread module configured to measure a line-spread function of the medical imaging system;
   wherein the angled edge module includes at least one cavity, and an insert provided in the at least one cavity, wherein the insert has a plurality of angled edges, and wherein the insert and the angled edge module are made of different materials; and
   wherein the modular phantom is configured to measure an imaging performance of the medical imaging system.

2. The modular phantom of claim 1, wherein the plurality of angled edges form a smooth, curved surface.

3. The modular phantom of claim 2, wherein the smooth, curved surface is hemispherical, elliptical or non-planar in cross section.

4. The modular phantom of claim 1, wherein at least two of the plurality of angled edges are placed at different angles.

5. The modular phantom of claim 1, wherein the plurality of angled edges form a polyhedron.

6. The modular phantom of claim 1, wherein a top surface of the insert is flat piece-wise and has a plurality of different facet angles formed by the plurality of angled edges.

7. The modular phantom of claim 1, wherein the angled edge module is configured to measure an edge-spread function for one or more contrast levels.

8. The modular phantom of claim 1, wherein the modular phantom includes at least two of a same module, and wherein the imaging performance and a dosimetry of the medical imaging system are measured using a same set of technique factors for the medical imaging system, wherein the same set of technique factors include one or more of an exposure time, a tube potential, a tube current, and a system geometry of the medical imaging system.

9. The modular phantom of claim 1, further comprising:
   one or more through holes configured to receive one or more instruments for measuring a dosimetry of the medical imaging system; and
   the one or more instruments include an ionization chamber.

10. The modular phantom of claim 1, wherein at least one of the cone-beam module or the line spread module includes a cavity adapted to receive an insert configured to measure the imaging performance of the medical imaging system, wherein the insert and a module comprising the insert are made of different materials, wherein the insert includes one of (a) at least two components stacked along a z-direction of the cone-beam module or (b) a slit extending along a central line of the insert.

11. A modular phantom for medical imaging comprising:
   at least one of a cone-beam module configured to measure a cone-beam artifact for a medical imaging system, an angled edge module configured to measure at least one of a spatial resolution or contrast properties of the medical imaging system, or a line spread module configured to measure a line-spread function of the medical imaging system;
   wherein the angled edge module includes at least one cavity, and an insert provided in the at least one cavity, wherein the insert has a smooth, curved surface, and wherein the insert and the angled edge module are made of different materials; and wherein the modular phantom is configured to measure an imaging performance of the medical imaging system.

12. The modular phantom of claim 11, wherein the smooth, curved surface is hemispherical, elliptical or non-planar in cross section.

13. The modular phantom of claim 11, wherein the modular phantom comprises one or more modules ordered according to a predetermined order.

14. A method for measuring properties associated with a medical imaging system using a modular phantom including one or more modules ordered according to a predetermined order, the one or more modules including at least one of a cone-beam module configured to measure a cone-beam artifact for the medical imaging system, an angled edge module configured to measure at least one of a spatial resolution or contrast properties of the medical imaging system, or a line spread module configured to measure a line-spread function of the medical imaging system, wherein the angled edge module includes at least one cavity, and an insert provided in the at least one cavity, wherein the insert has a plurality of angled edges, and wherein the insert and the angled edge module are made of different materials, the method comprising:
determining one or more properties associated with an imaging performance of the medical imaging system to be measured;
identifying the predetermined order of the one or more modules based on the one or more properties to be measured;
assembling the modular phantom based on the predetermined order;
placing the modular phantom between a detector and a radiation source of the medical imaging system;
collecting a first set of rays that are emitted from the radiation source on the detector after the first set of rays travel through the modular phantom; and
measuring the one or more properties associated with the imaging performance of the medical imaging system using the collected first set of rays.

15. The method of claim 14, wherein measuring the one or more properties associated with the medical imaging system includes:
measuring dosimetry of the medical imaging system using the collected first set of rays; or
measuring one or more of the spatial resolution, an image uniformity, an image noise, a contrast, a contrast-to-noise ratio, or the cone-beam artifact associated with the medical imaging system.

16. The method of claim 14, further comprising:
removing the modular phantom from the medical imaging system;
assembling the modular phantom based on a different predetermined order into a modified modular phantom;
placing the modified modular phantom between the detector and the radiation source of the medical imaging system;
collecting a second set of rays that are emitted from the radiation source on the detector after the second set of rays travel through the modified modular phantom;
measuring the one or more properties associated with the imaging performance of the medical imaging system using the collected second set of rays; and
measuring dosimetry of the medical imaging system using the collected second set of rays.

17. The method of claim 14, wherein plurality of angled edges form a smooth, curved surface that is hemispherical, elliptical or non-planar in cross section.

18. The method of claim 14, wherein at least two of the plurality of angled edges are placed at different angles.

19. The method of claim 14, wherein the plurality of angled edges form a polyhedron.

20. The method of claim 14, wherein a top surface of the insert is flat piece-wise and has a plurality of different facet angles formed by the plurality of angled edges.

* * * * *